United States Patent
Kramer et al.

(10) Patent No.: US 6,415,180 B1
(45) Date of Patent: Jul. 2, 2002

(54) DEVICE AND METHOD FOR VENTRICULAR TRACKING AND PACING

(75) Inventors: Andrew P. Kramer, Minneapolis, MN (US); Albert Maarse, Amstelveen (NL); Jeffrey E. Stahmann, Ramsey; Rene H. Wentkowski, White Bear Lake, both of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/420,679

(22) Filed: Oct. 19, 1999

Related U.S. Application Data

(63) Continuation-in-part of application No. 08/833,281, filed on Apr. 4, 1997, now Pat. No. 5,983,138.

(51) Int. Cl.⁷ .............................................. A61N 1/362
(52) U.S. Cl. ........................................................ 607/9
(58) Field of Search ..................................... 602/9, 14

(56) References Cited

U.S. PATENT DOCUMENTS

| | | | |
|---|---|---|---|
| 4,788,980 A | 12/1988 | Mann et al. | |
| 4,932,406 A | 6/1990 | Berkovits | 128/419 |
| 5,097,832 A * | 3/1992 | Buchanan | 607/14 |
| 5,103,820 A | 4/1992 | Markowitz | |
| 5,123,412 A | 6/1992 | Betzold | |
| 5,129,393 A | 7/1992 | Brumwell | |
| 5,342,405 A * | 8/1994 | Duncan | 607/9 |
| 5,441,523 A | 8/1995 | Nappholz | |
| 5,470,342 A | 11/1995 | Mann et al. | |
| 5,643,326 A * | 7/1997 | Weiner et al. | 607/14 |
| 5,713,928 A | 2/1998 | Bonnet et al. | |
| 5,741,309 A | 4/1998 | Maarse | |
| 5,792,193 A | 8/1998 | Stoop | 607/14 |

OTHER PUBLICATIONS

U Ellenboden, Kenneth A., "Cardiac Pacing", 263–308.

* cited by examiner

*Primary Examiner*—George R. Evanisko
(74) *Attorney, Agent, or Firm*—Nikolai & Mersereau, P.A.

(57) ABSTRACT

A device and method for multi chamber pacing a patient's heart having heart failure and intrinsic conduction, wherein ventricular tracking is used to pace the ventricle when the sinus rate exceeds a preset atrial maximum tracking rate. The ventricular tracking pacemaker increases the range of pacing the ventricle. The ventricular tracking minimizes the loss of ventricular pacing caused by intrinsic conduction when the sinus rate is below an atrial maximum tracking rate, and it induces a new ventricular pacing behavior for sinus rates above the atrial maximum tracking rate without any significant pacing hysteresis as the sinus rate returns towards the lower rate limit.

2 Claims, 19 Drawing Sheets

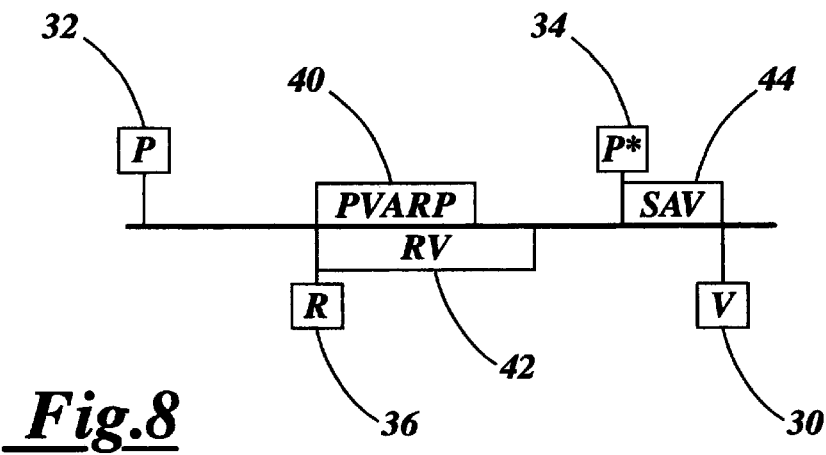
_Fig.8_
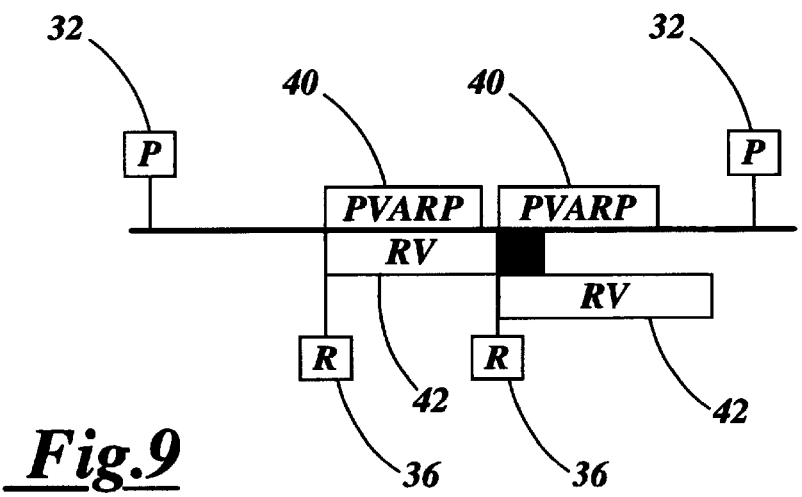
_Fig.9_
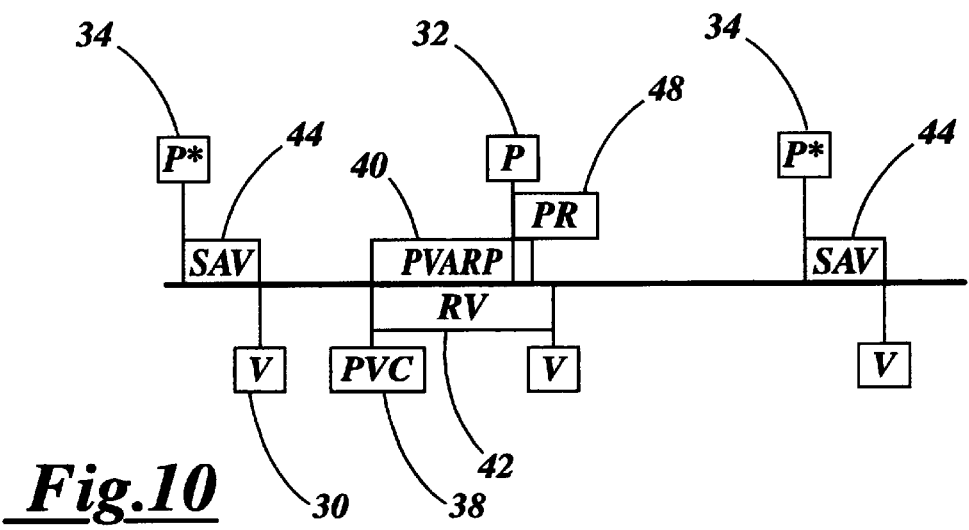
_Fig.10_

DEVICE AND METHOD FOR VENTRICULAR TRACKING AND PACING

The present application is a continuation-in-part application of application Ser. No. 08/833,281, filed on Apr. 4, 1997 and allowed on May 6, 1999, now U.S. Pat. No. 5,983,138 and entitled "DEVICE AND METHOD FOR VENTRICULAR TRACKING AND PACING".

BACKGROUND OF THE INVENTION

I. Field of the Invention

This invention relates generally to a device and method for pacing a patient's heart and more particularly to a device and method for improving the hemodynamic performance of patients suffering from heart failure through multi chamber pacing. The patient in need of improving hemodynamic performance may suffer from, for example, congestive heart failure (CHF), or other heart failure requiring pacing even though intrinsic PR conduction is present. The device includes a means for tracking an R-wave associated with intrinsic conduction in a ventricle of the patient's heart. The method includes tracking a sensed R-wave for a predetermined RV delay interval and then stimulating the ventricle if a P-wave is sensed during the preset simultaneous Post Ventricular Atrial Refractory Period (PVARP) interval.

II. Discussion of the Related Art

Typically, a patient suffering from a higher degree of AV-block or an AV conduction disorder is implanted with a conventional atrial tracking (DDD or VDD) pacemaker suited for pacing the ventricle. Such a pacemaker is designed to pace the ventricle after a pre-set AV delay, synchronous with the intrinsic atrial rate. The purpose of these pacemakers is to make sure that heart beats are properly timed and not omitted. Intrinsic rhythm is favorable over paced rhythm for both hemodynamic and economic (battery conservation) reasons. It is also important and necessary to prevent pacing the ventricle during the vulnerable period for inducing arrhythmia immediately following an intrinsic ventricular beat. Hence, ventricular pacing is inhibited when intrinsic conduction from the SA node causes an R-wave to be sensed prior to the scheduled ventricular pace.

Patients suffering from congestive heart failure (CHF), for example, either do not exhibit heart block at all or often only suffer from a first degree AV-block or a slightly prolonged delay interval between the depolarization of the atrium and the depolarization of the ventricle. Recent research has shown that acute hemodynamic performance, exercise tolerance and quality of life of CHF patients can be improved by a pre-excitation of the ventricles with pacing following normal sinus beats. Patients benefiting from pre-excitation of the ventricles experience a return of heart failure symptoms immediately upon omission of pre-excitation pacing. Thus, for these patients, it is important that the paced pre-excitation of the ventricle be performed continuously in order to improve the contraction pattern, even though intrinsic beats would occur slightly later if there were no pacing. When pacing a patient suffering from CHF, it is highly undesirable to omit pacing when it is supposed to occur.

When pacing the heart of a CHF patient having normal intrinsic (PR) conduction, although continuous pacing is desirable, use of a conventional atrial tracking dual chamber pacemaker completely inhibits ventricular pacing when the intrinsic atrial rate (hereinafter the sinus rate) rises above a preprogrammed atrial maximum tracking rate (AMTR). These pacemakers also exhibit an undesirable pronounced pacing hysteresis, wherein ventricular pacing is not resumed until the sinus rate falls below a ventricular inhibition threshold rate (VIR). Also, in these pacemakers, a premature ventricular contraction (PVC) may inhibit ventricular pacing when the sinus rate exceeds the VIR.

It would be advantageous to eliminate the pacing hysteresis, while extending the limit or MTR for pacing of the ventricle. However, this is not possible with the conventional atrial tracking multi-chamber pacemaker. A CHF patient, for example, has an elevated sinus rate in order to maintain normal cardiac output despite reduced cardiac pumping efficiency and, therefore, requires a high atrial MTR. Together with an elevated sinus rate, many such patients also have prolonged PR intervals and correspondingly prolonged retrograde conduction intervals requiring long PVARP intervals. The required long PVARP intervals prevent tracking of retrograde P-waves, thereby reducing pacemaker mediated tachycardia (PMT). In conventional atrial tracking pacemakers, the highest allowable atrial MTR is determined in part by the length of the PVARP interval, which may limit the atrial MTR to a rate that is below the normal range of sinus rates in the CHF patient. Hence, use of a conventional atrial tracking dual chamber pacemaker would not allow continuous ventricular pacing above the atrial MTR. Therefore, there is a need for a dual chamber pacemaker and a method of operating the same that may be used to pace the failing heart of a patient having intrinsic conduction, wherein the pacemaker provides for continuous pacing of the ventricle at a sinus rate that exceeds an atrial maximum tracking rate and does not exhibit pacing hysteresis below the MTR. The present invention addresses this need.

SUMMARY OF THE INVENTION

The purpose of the present invention is to provide a device and method of pacing continuously, without hysteresis, the ventricles of a patient's failing heart having intrinsic conduction even when the sinus rate rises above a preset atrial maximum tracking rate.

Conventional dual chamber pacemakers commonly have a combination of dual chamber sensing, atrial sensing, ventricular sensing, dual chamber pacing, atrial pacing, ventricular pacing, and atrial tracking. A conventional dual chamber pacemaker may be modified according to the present invention to include a ventricular tracking mode and thereby increase the range of pacing therapy. When used with a patient having intrinsic (PR) conduction, the ventricular tracking mode minimizes the loss of ventricular pacing output as the sinus rate rises above a preset atrial MTR. As the atrial MTR is exceeded by the sinus rate, the ventricular tracking pacemaker restores a Wenckebach-like pacing behavior, thereby continuing ventricular pacing. Those skilled in the art will appreciate that this pacing, although similar to Wenckebach pacing behavior is not Wenckebach pacing.

During this Wenckebach-like pacing, the ventricular tracking pacemaker paces the ventricle due to atrial tracking unless a legitimate P-wave is sensed during a preset post ventricular atrial refractory period (PVARP). A legitimate P-wave refers to a signal or wave that corresponds to an intrinsic atrial depolarization. When a legitimate P-wave is sensed during the PVARP, the ventricular tracking pacemaker tracks a preceding sensed R-wave (due to intrinsic PR conduction) and paces the ventricle after a preset delay interval, hereinafter referred to as the RV delay. Alternatively the ventricular pace can occur after a preset delay from the P-wave sensed during PVARP, hereinafter referred to as the refractory atrial to ventricular (RAV) delay. As the sinus rate continues to increase, the sinus rate reaches a 2:1 ventricular tracking rate up to a ventricular MTR or limit at which point ventricular pacing is inhibited. The conventional dual chamber pacemaker ignores legitimate P-waves sensed during PVARP and does not pace the ventricle above the atrial MTR. With the ventricular tracking pacemaker, as the sinus rate decreases from the ventricular MTR, there is no significant pacing hysteresis commonly found in the conventional atrial tracking pacemakers.

The ventricular tracking pacemaker includes a means for sensing an atrial event and transmitting a signal associated with the sensed atrial event, means for sensing a ventricular event and transmitting a signal associated with the sensed ventricular event, means for tracking a P-wave, means for tracking an R-wave, means for selectively stimulating a preselected ventricle of the patient's heart, and a means for controlling the selective stimulation of the ventricle. The means for controlling the stimulation is electrically coupled to the sensing, tracking and stimulating means. The means for controlling the stimulation controls the stimulation to the preselected ventricle in accordance with a timing sequence which is dependent upon the tracked ventricular and tracked atrial events.

In the preferred embodiment, the means for controlling determines the intrinsic ventricular rate from the signal corresponding to sensed ventricular events. If the intrinsic ventricular rate is greater than the preset ventricular maximum tracking rate, the means for controlling inhibits the stimulation to the ventricle.

OBJECTS

It is accordingly a principal object of the present invention to provide a multi chamber pacemaker for pacing the selected ventricles of a patient suffering from heart failure but having intrinsic PR conduction, wherein the ventricle may be paced at a rate that is above an atrial maximum tracking rate.

A further object of the present invention is to provide a multi chamber pacemaker for pacing the selected ventricles of a patient, wherein the selected ventricles are paced a preset time after an R-wave is tracked by the pacemaker.

Another object of the present invention is to provide a method of multi chamber pacing that paces the selected ventricles a preset time after detecting an intrinsic conduction transmitted from the ventricles.

Yet another object of the present invention is to provide a method of multi chamber pacing which paces the ventricles a preset time after a P-wave is sensed during a PVARP interval following a sensed R-wave, wherein pacemaker-mediated tachycardia is prevented if the P-wave is due to retrograde conduction.

Still another object of the present invention is to provide a pacemaker that may pace the ventricle above the atrial MTR, wherein there is no significant pacing hysteresis when the atrial rate returns to a lower rate limit.

These and other objects, as well as these and other features and advantages of the present invention will become readily apparent to those skilled in the art from a review of the following detailed description of the preferred embodiment in conjunction with the accompanying drawings and claims and in which like numerals in the several views refer to corresponding parts.

BRIEF DESCRIPTION OF THE DRAWINGS

FIG. 8 is a plot showing a tracked R-wave in conjunction with a ventricular tracking pacemaker's PVARP and RV intervals, wherein a P-wave is neither sensed nor tracked during the RV interval;

FIG. 9 is a plot showing a tracked R-wave in conjunction with a ventricular tracking pacemaker's PVARP and RV intervals, wherein a second R-wave is tracked during the RV interval;

FIG. 10 is a plot showing a sensed P-wave and tracked PVC in conjunction with a ventricular tracking pacemaker's PVARP and RV intervals;

DEFINITIONS

| | |
|---|---|
| PVC | Premature Ventricular Contraction |
| LRL | Lower Rate Limit |
| PVARP | Post Ventricular Atrial Refractory Period |
| PR | time between depolarization of the atrium and ventricle |
| VIR | Ventricular Inhibition Rate |
| AMTR | Atrial Maximum Tracking Rate |
| VMTR | Ventricular Maximum Tracking Rate |
| CHF | Congestive Heart Failure |
| SAV | Sensed Atrial to Ventricular delay |
| RAV | Refractory Atrial to Ventricular delay |
| RV | time delay between sensing ventricular conduction and pacing the ventricle |
| URL | Upper Rate Limit |
| MTR | Maximum Tracking Rate |
| S-PVARP | Sensed Post Ventricular Atrial Refractory Period—PVARP dependant upon a sensed R-wave |
| MHI | Middle Hysteresis Interval |
| MHIR | Middle Hysteresis Interval Rate |
| S-VA | sensed VA interval |
| PAV | paced atrial to ventricular delay |
| AV | atrial-ventricular pacing delay |

DETAILED DESCRIPTION

Figure 1:
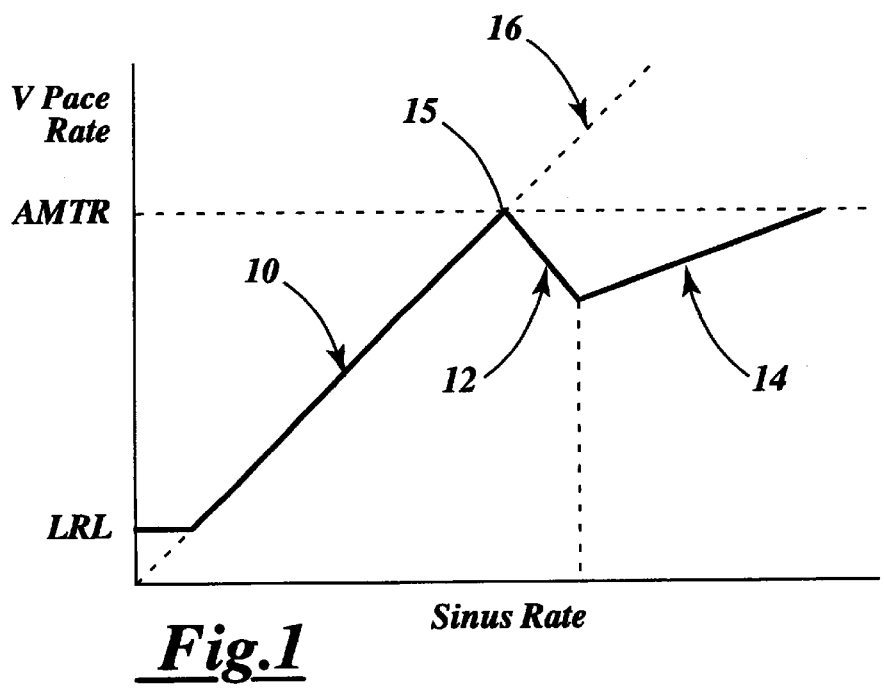
FIG. 1 is a graph showing the intrinsic atrial (sinus) rate in relation to the paced ventricular rate of a conventional atrial tracking pacemaker, employed when a patient has complete heart block.
Figure 2:
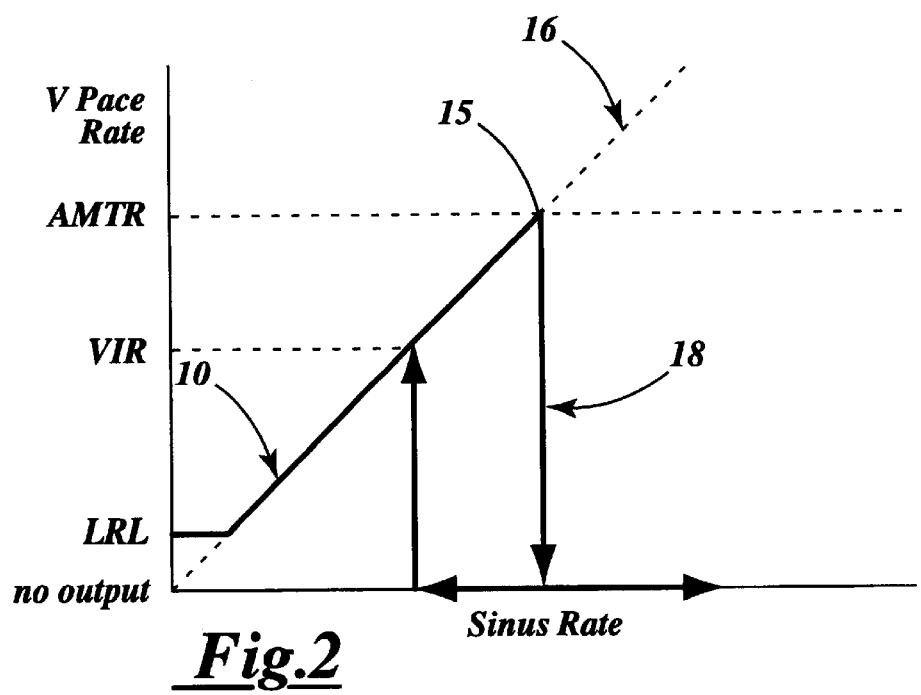
FIG. 2 is a graph showing the intrinsic atrial rate in relation to the paced ventricular rate of a conventional atrial tracking pacemaker where the patient has normal intrinsic (PR) conduction.
Figure 3:
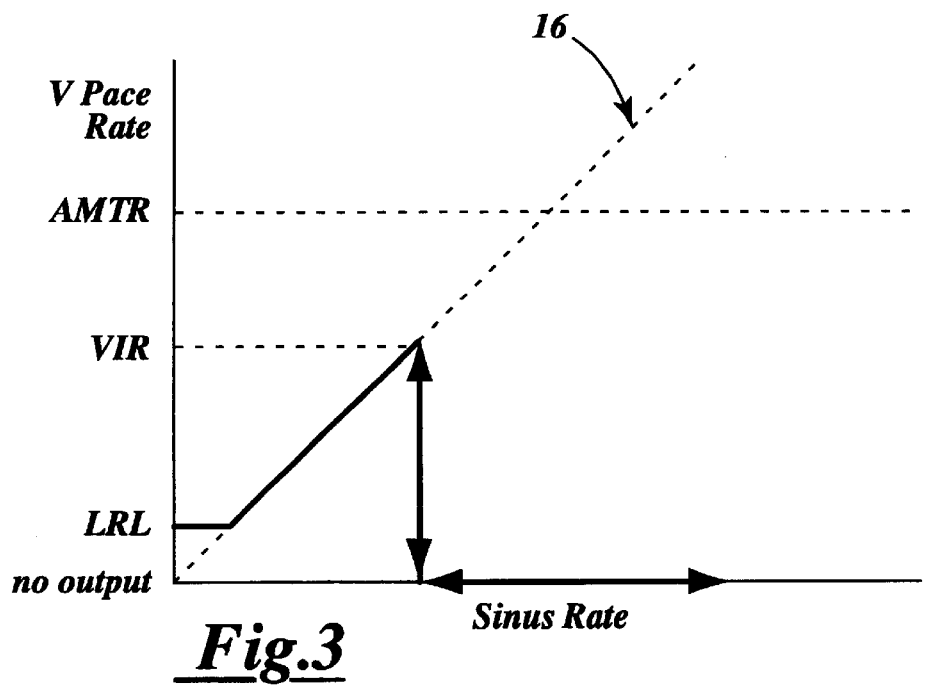
FIG. 3 is a graph showing the intrinsic atrial rate in relation to the paced ventricular rate of a conventional atrial tracking pacemaker where the patient has experienced a Premature Ventricular Contraction (PVC)

Referring first to FIGS. 1–3, these graphs show the intrinsic atrial rate or sinus rate of a patient in relation to the paced ventricular rate or output of a conventional atrial tracking pacemaker when used in a variety of patient conditions. FIG. 1 illustrates the ventricular pacing rate by a conventional atrial tracking pacemaker, pacing the heart of a patient having a complete block of all intrinsic conduction. As the sinus rate increases, the pacemaker's pacing rate tracks the atrial rate until the pacing rate reaches a pre-programmed atrial maximum tracking rate (AMTR) at 15. At this point, as the atrial rate continues to increase, there is a fall-off in the ventricular pacing rate attributable to a pacemaker mediated atrial Wenckebach behavior at 12. During this period, some of the pacemaker's ventricular pacing pulses are inhibited by the pacemaker to prevent pacing the ventricle at a rate above the AMTR. As the sinus rate at 16 continues to increase above the AMTR, the average ventricular pacing rate slowly decreases until a 2:1 ratio between the atrial rate and ventricular pacing occurs, as at 14.

FIG. 2 illustrates the pacing behavior of a conventional atrial tracking pacemaker, when the patient's heart has normal intrinsic (PR) conduction. The ventricular pacing rate tracks the intrinsic atrial rate until the atrial rate reaches an AMTR as at 15. Once the sinus rate exceeds the pre-programmed AMTR, the pacemaker inhibits ventricular pacing until the intrinsic atrial rate decreases to a rate below the AMTR corresponding with the Ventricular Inhibition Rate (VIR). The VIR is equal to the rate corresponding to the sum of the PVARP and PR intervals. When the sinus rate decreases to a rate equal to the VIR, ventricular pacing resumes until the intrinsic atrial rate again reaches the AMTR. As seen in FIG. 2, when pacing a patient (having intrinsic conduction) with a conventional atrial tracking pacemaker, there is a pronounced pacing hysteresis as represented at 18. This pacing hysteresis limits the range of pacing therapy to the patient. Unlike pacing a patient having complete heart block, the atrial tracking pacemaker will not pace a patient having intrinsic conduction when the sinus rate exceeds the AMTR. This is significant because many of the patients having intrinsic conduction who could benefit from uninterrupted ventricular pacing typically have elevated sinus rates (above the AMTR) to compensate for the reduced pumping efficiency of their failing heart.

Additionally, when the patient's heart has intrinsic conduction, the ventricular pacing rate by the pacemaker may even be inhibited at a rate below the AMTR. FIG. 3 illustrates that the range of pacing therapy of a conventional atrial tracking pacemaker may be further limited by a premature ventricular contraction (PVC). When a PVC occurs, and the sinus rate is above the VIR, ventricular pacing may be inhibited by the atrial tracking pacemaker until the sinus rate falls below the VIR, thereby further limiting the range of available pacing therapy.

Figure 4:
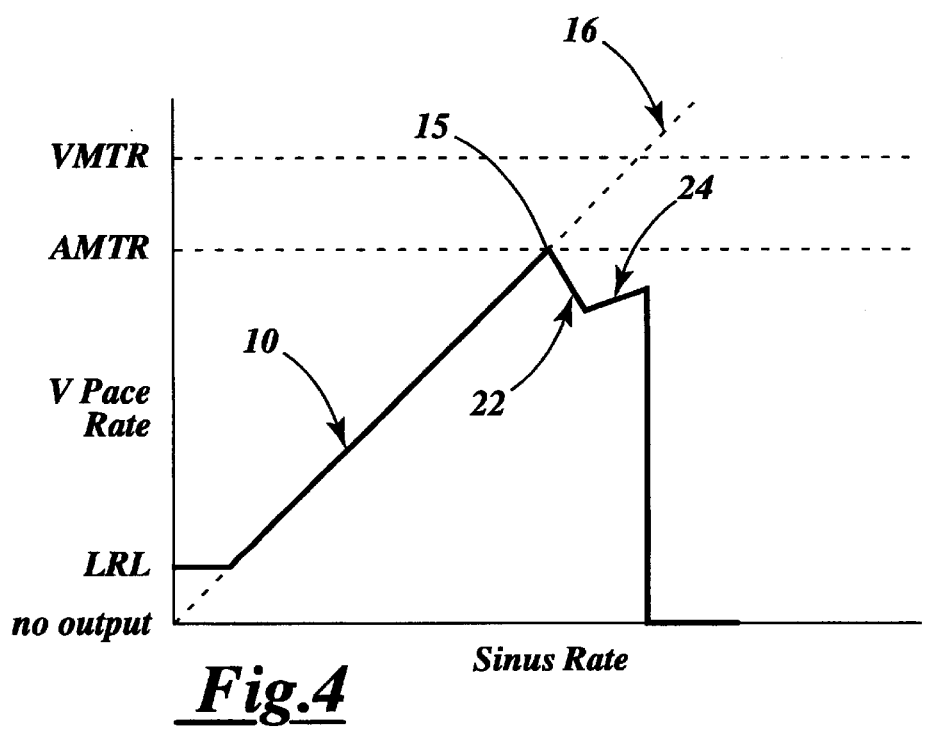
FIG. 4 is a graph showing the intrinsic atrial rate in relation to the paced ventricular rate of a ventricular tracking pacemaker where the patient has normal intrinsic (PR) conduction.
Figure 5:
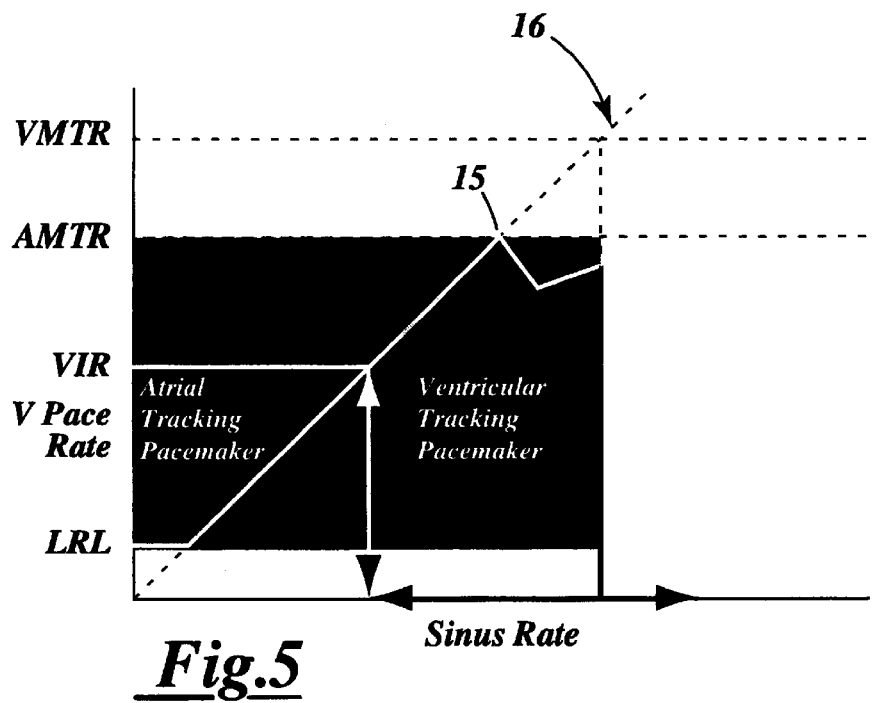
FIG. 5 is a comparison graph illustrating the increased range of pacing therapy utilizing a ventricular tracking pacemaker compared to the conventional atrial tracking pacemaker.

Referring to FIGS. 4 and 5, the sinus rate of a patient having normal intrinsic conduction is shown in relation to the resulting paced ventricular rate of a ventricular tracking pacemaker of the present invention. Significantly, the range of pacing therapy is expanded using a ventricular tracking pacemaker of the present invention on a patient having intrinsic conduction. When the sinus rate exceeds a preset atrial maximum tracking rate (AMTR) as at 15, ventricular tracking restores a Wenckebach-like behavior at 22 (hereinafter referred to as ventricular Wenckebach; those skilled in the art will appreciate, however, the distinction between this behavior and the behavior known as Wenckebach behavior). During ventricular Wenckebach-like pacing behavior, ventricular pacing occurs due to atrial tracking, until a sensed atrial event falls within the preset PVARP allowing an intrinsically conducted R-wave to occur, which inhibits ventricular pacing for that sinus beat. To restore ventricular pacing when the sensed atrial event falls within the preset PVARP, the subsequent intrinsically conducted R wave is tracked and the ventricle is paced after a preset pacing delay, subject to other variables discussed in further detail below. As the sinus rate (represented by dotted line 16) increases above the AMTR as at 15, the average ventricular pacing rate slowly decreases due to Wenckebach-like pacing at 22 until the sinus rate reaches a 2:1 ventricular tracking rate as at 24. Once the sinus rate exceeds the preset ventricular maximum tracking rate (VMTR), ventricular pacing is inhibited. Importantly, unlike the resulting behavior of an atrial tracking pacemaker, there is no significant hysteresis as the sinus rate falls below the VMTR or AMTR of the ventricular tracking pacemaker.

FIGS. 6–22 are various plots illustrating the occurrence of a sensed P-wave and the resulting tracked R-wave plotted over time with respect to the ventricular tracking pacemaker's preset timing intervals and varying sinus rates. The time of occurrence of the ventricular pacing stimulation is indicated by labeled block "V" at 30. The time of occurrence of a sensed P-wave is indicated by labeled block "P" at 32. A tracked P-wave is indicated by labeled block "P" at 34. A time of occurrence of a sensed R-wave due to intrinsic conduction is indicated by labeled block "R" at 36 and a time of occurrence of a sensed PVC is indicated by labeled block "PVC" as at 38 and the time of occurrence of a sensed retrograde P-wave (Retro P) is indicated at 46 (see FIGS. 10–12, 14, and 16). Several preset timing intervals are positioned relative to the time at which the P wave, R-wave or a PVC are sensed. The preset post ventricular atrial refractory period (PVARP) timing interval is indicated at 40, the preset ventricular pacing delay interval (RV) at 42, the sensed atrial to ventricular delay (SAV) at 44, the intrinsic conduction (PR) interval is indicated at 48, the preset atrial maximum tracking rate interval (AMTRI) is indicated at 50 and the preset refractory atrial to ventricular delay (RAV) is indicated at 51.

Two alternative timing sequences of the ventricular tracking pacemaker are illustrated by the various Figures. Only one timing sequence can be in effect during a particular cardiac cycle, however, those skilled in the art will appreciate that alternative timing sequences can be used on different cardiac cycles. The choice and use of the alternate timing sequence is programmable in the ventricular tracking pacemaker. The first timing sequence, referred to as the "rate priority" timing sequence or "rate priority" ventricular tracking, paces the ventricles after a tracked R-wave at a preset ventricular tracking rate. An alternate timing sequence, referred to as the "delay priority" timing sequence or "delay priority" ventricular tracking, paces the ventricles after a tracked R-wave to achieve a preset delay between a refractory P-wave sense and the ventricular pace, but not faster than a preset ventricular tracking rate. The delay priority timing sequence is an alternate of the more general rate priority timing sequence. As further described below, FIGS. 6–18 illustrates the general "rate priority" timing sequence, which applies also to "delay priority" ventricular tracking, except that the ventricular tracking rate is not constant for "delay priority" timing. FIGS. 19–22 illustrate the alternate "delay priority" timing sequence.

Figure 6:
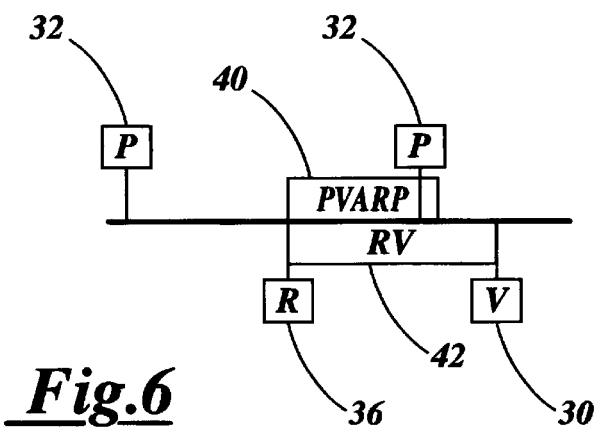
FIG. 6 is a plot showing a sensed P-wave and tracked R-wave in conjunction with a ventricular tracking pacemaker's PVARP and RV intervals.
Figure 7:
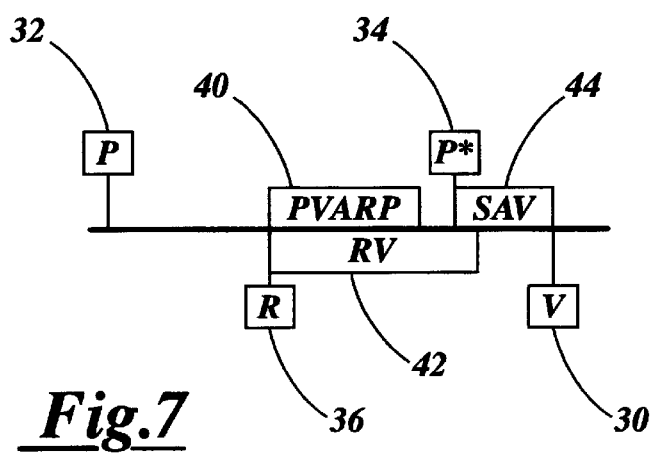
FIG. 7 is a plot showing a sensed P-wave and tracked R-wave in conjunction with a ventricular tracking pacemaker's PVARP and RV intervals, wherein a P-wave is tracked during the RV interval.

Referring to FIG. 6, the rate priority timing sequence of the ventricular tracking pacemaker is illustrated. An R-wave 36 is sensed, initiating the PVARP 40 and RV 42 intervals. Since a P-wave 32 is sensed during the PVARP 40 interval, the ventricle is paced after a tracked RV delay 42. If a P-wave 34 is sensed after the PVARP 40 but before the expiration of the RV 42 delay, then the ventricle is not paced until the expiration of a sensed atrial to ventricular delay 44 as shown in FIG. 7. Further, when a P-wave 32 is not sensed during the PVARP 40 interval, the ventricle is not paced at the end of the RV 42 interval, (see FIG. 8). Also, if an R-wave 36 is sensed during the RV delay 42 interval, then the RV delay 42 interval is restarted (see FIG. 9). Hence, normally the ventricle will be paced according to rate priority ventricular tracking a predetermined amount of time after an R-wave is sensed if a P-wave is also sensed during a PVARP and RV interval, unless other conditions are present.

Figure 11:
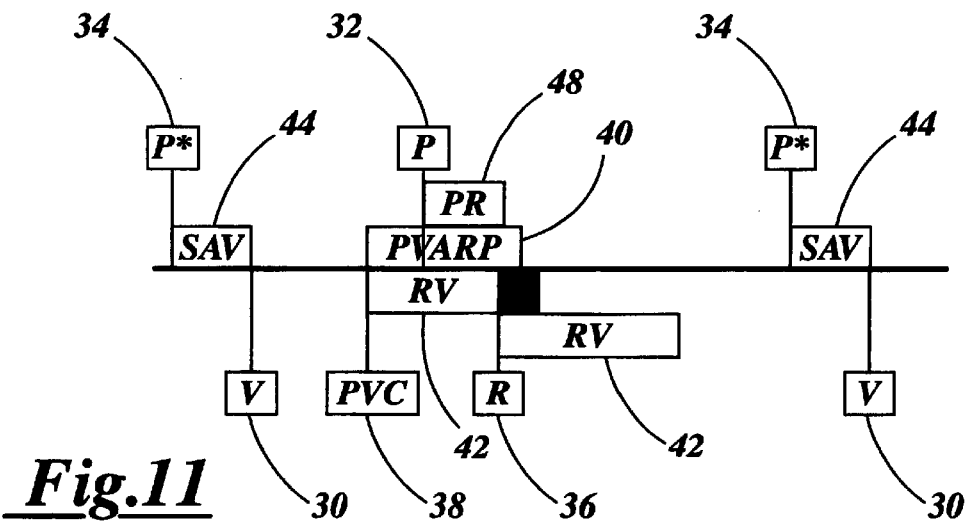
FIG. 11 is a plot showing a sensed P-wave and tracked PVC in conjunction with a ventricular tracking pacemaker's PVARP and RV intervals, wherein a second R-wave is tracked during the RV interval.
Figure 12:
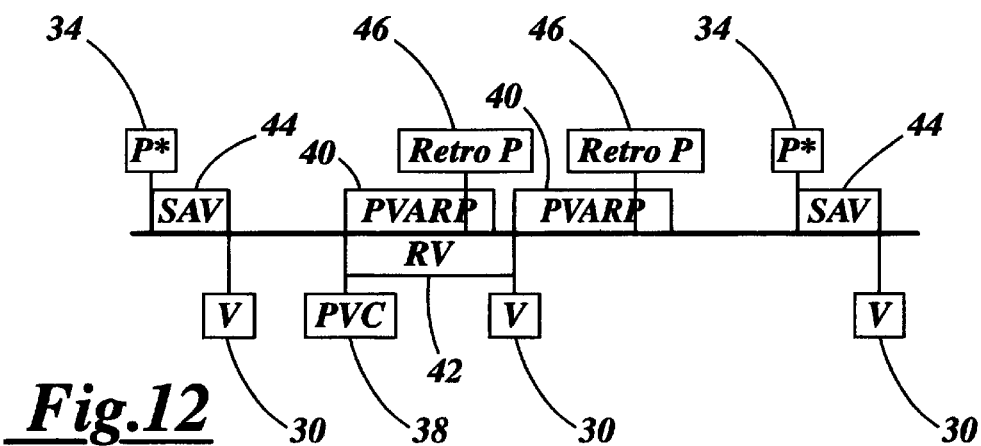
FIG. 12 is a plot showing a sensed retrograde P-wave and tracked PVC in conjunction with a ventricular tracking pacemaker's PVARP and RV intervals.

FIGS. 10–12 show the tracking behavior of the ventricular tracking pacemaker when the sinus rate is between the lower rate limit (LRL) and the ventricular inhibition rate (VIR). When the sinus rate is in this range, the ventricular tracking pacemaker may be programmed to pace the ventricle according to 1:1 atrial tracking, unless a PVC causes a sensed P-wave to fall in PVARP or causes a sensed retrograde P-wave within PVARP. In such a case, when a PVC causes a sensed P-wave to fall in PVARP or causes a sensed retrograde P-wave within PVARP, ventricular tracking takes over for pacing of the ventricle. FIG. 10 illustrates a sensed PVC 38 starting the preset PVARP 40 and RV delay 42. Since a legitimate P-wave 32 is sensed during the PVARP 40 and the intrinsic PR 48 conduction delay extends beyond the RV delay 42, the ventricle is paced at the end of the RV delay 42 interval. FIG. 11 illustrates a PVC causing a sensing of an R-wave 36 during the RV delay 42 interval and restarting of the RV delay 42 interval. When the sinus rate is between the lower rate limit (LRL) and the ventricular inhibition rate (VIR), a PVC 38 may cause a sensed retrograde P-wave 46. As shown in FIG. 12, a PVC cannot cause a pacemaker mediated tachycardia due to ventricular tracking. The PVC starts an RV 42 interval and the sensed retrograde P-wave 46 enables a ventricular tracking pace at 30, which in turn causes a second retrograde P-wave that is not followed by a ventricular pace because a second RV 42 interval is not initiated at the ventricular 30 pace.

Figure 13:
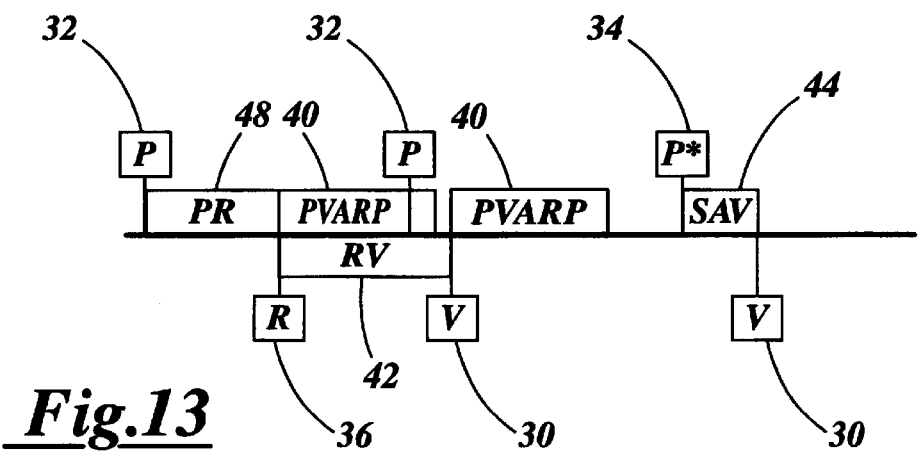
FIG. 13 is a plot showing a sensed P-wave and tracked R-wave in conjunction with a ventricular tracking pacemaker's PVARP and RV intervals, wherein the sinus rate is between the VIR and AMTR.
Figure 14:
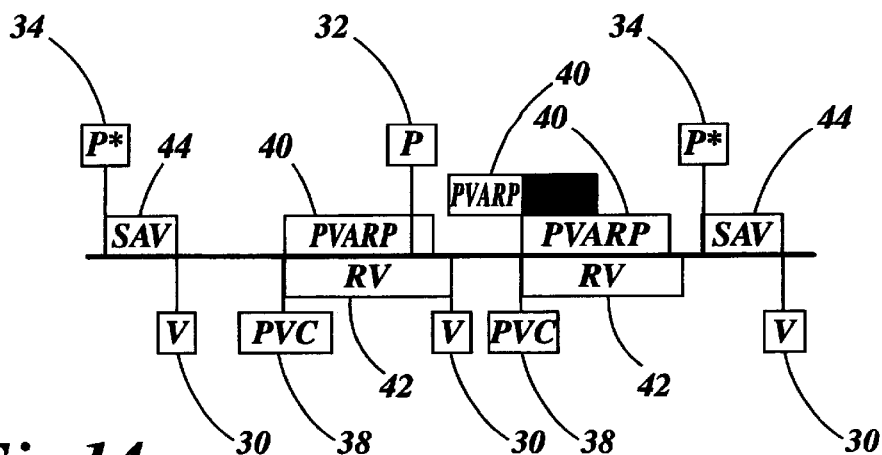
FIG. 14 is a plot showing a sensed P-wave and tracked PVC in conjunction with a ventricular tracking pacemaker's PVARP and RV intervals, wherein the sinus rate is between the VIR and AMTR.

Referring now to FIGS. 13 and 14, these plots illustrate the general reaction of the ventricular tracking pacemaker when the sinus rate is between the ventricular inhibition rate and the atrial MTR. Again in this rate range the ventricular tracking pacemaker may pace the ventricle in accordance with 1:1 atrial tracking, however since a single PVC 38 could cause continuous inhibition of ventricular pacing, it is necessary to pace the ventricle in accordance with ventricular tracking, unless a P-wave 34 is sensed outside of the PVARP 40. When an R-wave 36 due to intrinsic PR 48 conduction is sensed, wherein the sinus rate is greater than the ventricular inhibition rate, the ventricular tracking is triggered to restore ventricular pacing. A sensed R-wave 36 and P-wave 32 during PVARP 40 causes the pacing of the ventricle after the preset RV delay 42 (see FIG. 13). When a PVC is sensed and causes the intrinsic P-wave to be sensed during PVARP, ventricular tracking is triggered (see FIG. 14). If a PVC occurs such that a P-wave is sensed outside the PVARP, pacing of the ventricle after the RV delay is inhibited and normal atrial tracking occurs (see FIG. 14). Hence, it can be seen that in this rate range the ventricular tracking pacemaker differs from a conventional DDD, pacemaker. While a single PVC can cause an atrial tracking pacemaker to inhibit ventricular pacing, the ventricular tracking pacemaker will pace the ventricle after the RV delay as described above.

Figure 15:
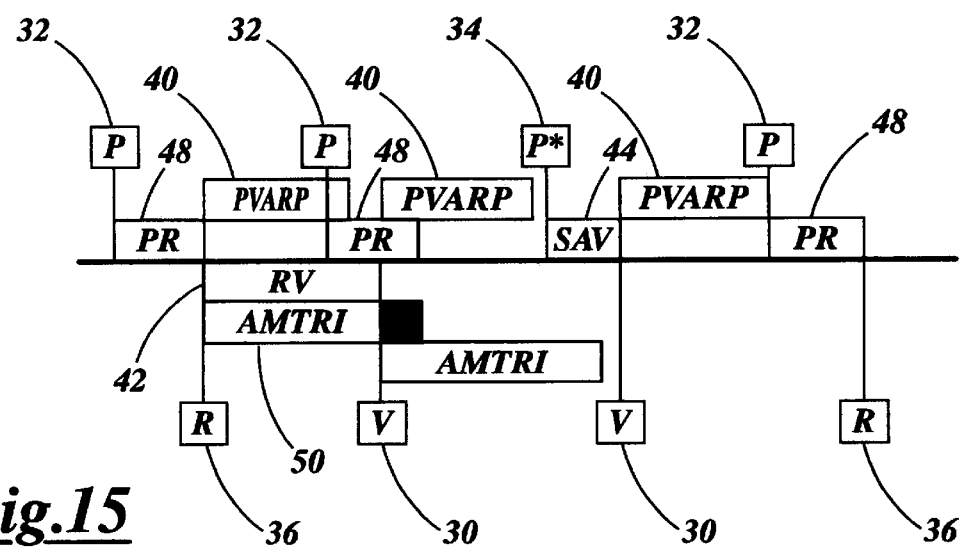
FIG. 15 is a plot showing a sensed P-wave and tracked R-wave in conjunction with a ventricular tracking pacemaker's PVARP and RV intervals, wherein the sinus rate is between the AMTR and VMTR.
Figure 16:
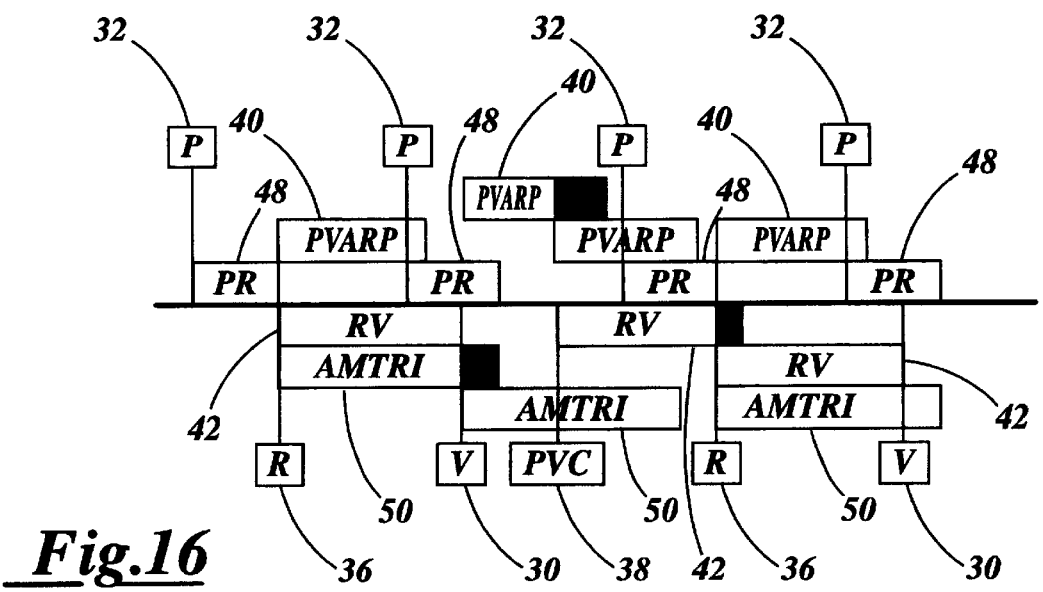
FIG. 16 is a plot showing a sensed P-wave and tracked PVC in conjunction with a ventricular tracking pacemaker's PVARP and RV intervals, wherein the sinus rate is between the AMTR and VMTR.
Figure 17:
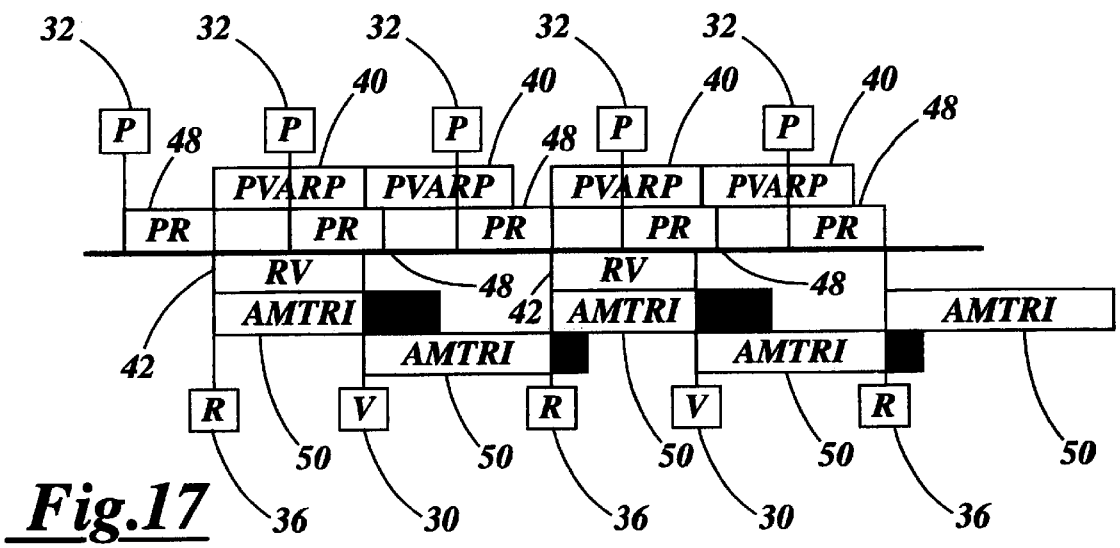
FIG. 17 is a plot showing a sensed P-wave and tracked R-wave in conjunction with a ventricular tracking pacemaker's PVARP and RV intervals, wherein the sinus rate is between the AMTR and VMTR and the ventricular tracking reaches a 2:1 blocking point.
Figure 18:
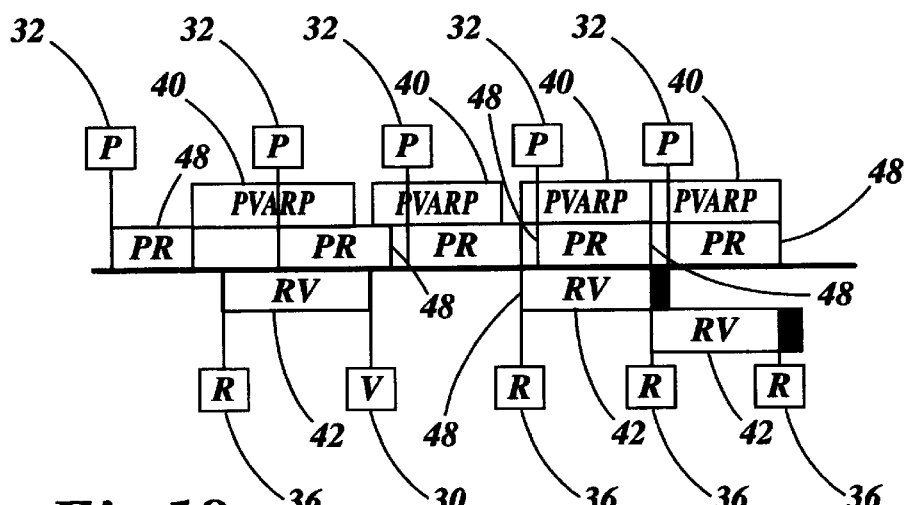
FIG. 18 is a plot showing a sensed P-wave and tracked R-wave in conjunction with a ventricular tracking pacemaker's PVARP and RV intervals, wherein the sinus rate exceeds the VMTR.

FIGS. 15–17 show the general tracking behavior of the ventricular tracking pacemaker when the sinus rate is between the atrial MTR (AMTR) and the ventricular maximum tracking rate (VMTR). When the sinus rate is in this range, the pacer goes into a ventricular Wenckebach-like pacing behavior, during which an intrinsically conducted R-wave occasionally inhibits a ventricular pace. The ventricular tracking pacemaker will continue to generate Wenckebach ventricular pacing behavior as long as the RV interval is less than the AMTRI (see FIG. 15). FIG. 16 shows that a PVC in this range can cause an extra Wenckebach cycle, wherein the ventricular tracking eventually restores ventricular pacing. Eventually, ventricular tracking reaches a 2:1 ventricular rate tracking (see FIG. 17). As illustrated in FIG. 18, once the sinus rate exceeds the VMTR, ventricular pacing is inhibited, because every RV interval is restarted by an intrinsic R wave before pacing can occur.

Figure 19:
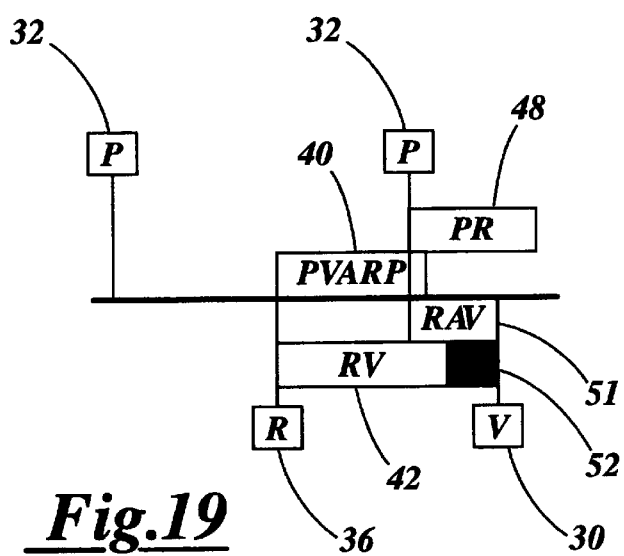
FIG. 19 is a plot showing a sensed P-wave and tracked R-wave in conjunction with a ventricular tracking pacemaker's PVARP, RV, and RAV intervals, when delay priority timing is in effect.

FIGS. 19–22 illustrate the alternate timing sequence of the ventricular pacemaker that dynamically extends the time of ventricular pacing after the RV delay expires, to thereby maintain a preset delay between the atrial sense and ventricular pace due to ventricular tracking. This timing sequence of the ventricular pacemaker is referred to as delay priority ventricular tracking and is illustrated generally in FIGS. 19 and 20. An R-wave 36 is sensed, initiating the PVARP 40 and RV 42 intervals. When a P-wave 32 is sensed during the PVARP 40 interval, a preset refractory atrial to ventricular delay (RAV) is initiated. As shown in FIG. 19, when the RV 42 interval ends before the expiration of the RAV 51 delay, the ventricle is paced at the end of the RAV 51 delay, as long as the RAV 51 delay is less than the intrinsic PR 48 interval. This has the effect of extending the duration of the RV 42 interval by the RV extension 52 period indicated by the highlighted portion of the box.

Figure 20:
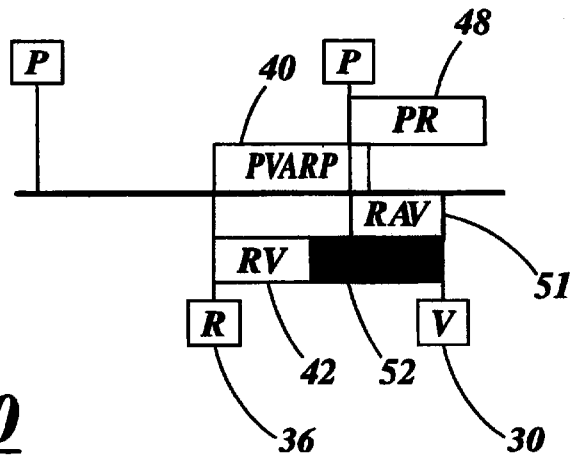
FIG. 20 is a plot showing a sensed P-wave and tracked R-wave in conjunction with a ventricular tracking pacemaker's PVARP, RV, and RAV intervals, when delay priority timing is in effect and a P-wave is sensed during the PVARP interval and after the RV interval.

FIG. 20 illustrates the delay priority timing sequence when the P-wave 32 is sensed during the PVARP 40 interval after the tracked RV delay 42 has ended. The RV delay 42 ends without pacing the ventricle because the P-wave 32 is not sensed during the RV delay 42. Instead, the ventricle is paced after the expiration of the RAV 51 interval, which is initiated by the P-wave 32 sensed during the PVARP 40 interval. Again, this has the effect of extending the duration of the RV 42 interval by the RV extension period.

Figure 21:
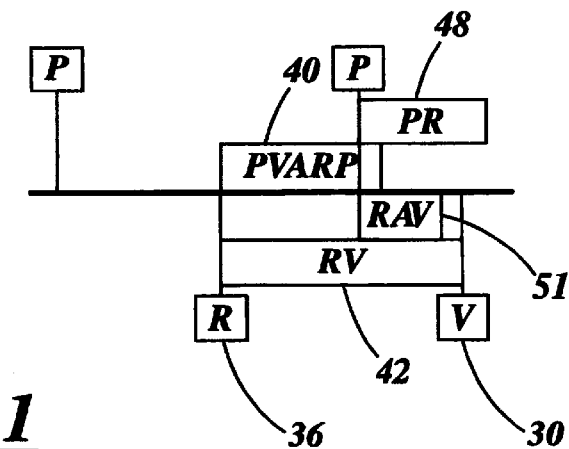
FIG. 21 is a plot showing a sensed P-wave and tracked R-wave in conjunction with a ventricular tracking pacemaker's PVARP, RV, and RAV intervals, wherein the RAV interval expires before the RV interval.
Figure 22:
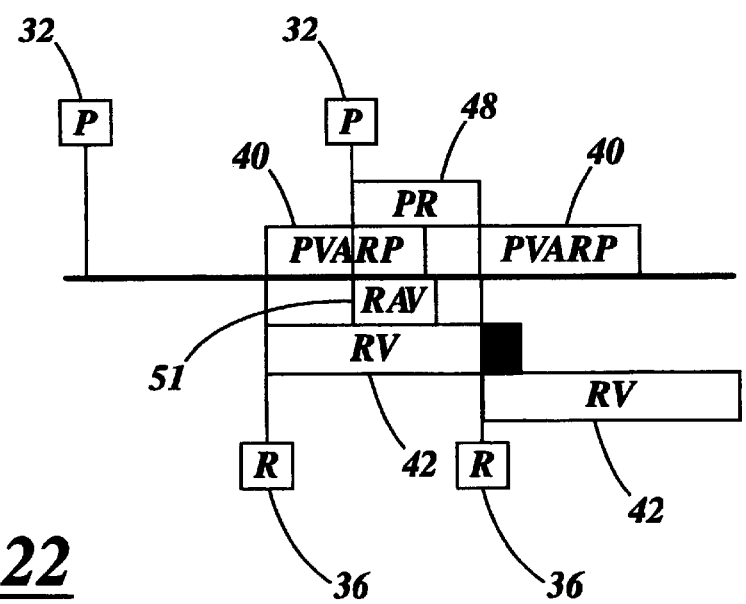
FIG. 22 is a plot showing a sensed P-wave and tracked R-wave in conjunction with a ventricular tracking pacemaker's PVARP, RV, and RAV intervals, wherein the RAV interval expires before the RV interval and a second R-wave is tracked during the RV interval.

FIGS. 21 and 22 illustrate that the delay priority timing sequence reverts to the rate priority timing sequence when the delay priority timing sequence would result in pacing the ventricle before the end of the RV interval. As shown in FIG. 21, an R-wave 36 is sensed, initiating the PVARP 40 and RV 42 intervals. When a P-wave is sensed during the PVARP 40 interval, the RAV 51 delay is initiated. Since the RAV 51 delay ends before the RV 42 interval, the ventricle is paced after the RV 42 interval, as long as it expires before the intrinsic PR 48 interval expires. When the RV 42 interval expires after the intrinsic PR 48 interval, as illustrated in FIG. 22, an intrinsic R-wave 36 is detected, which restarts the RV 42 interval.

Hence, the ventricle will be paced according to delay priority ventricular tracking a predetermined amount of time after a P-wave is sensed during PVARP following an R-wave, but not faster than the RV delay, unless other conditions are present. Those skilled in the art will appreciate that since delay priority ventricular tracking only has the effect of extending the RV interval, all the rate priority timing sequences shown in FIGS. 6–18 also apply to the ventricular pacemaker having a delay priority timing sequence when the RV interval in those Figures is replaced by an extended RV interval (the RV interval plus RV extension period) when it applies as shown in FIGS. 19 and 20.

Figure 23:
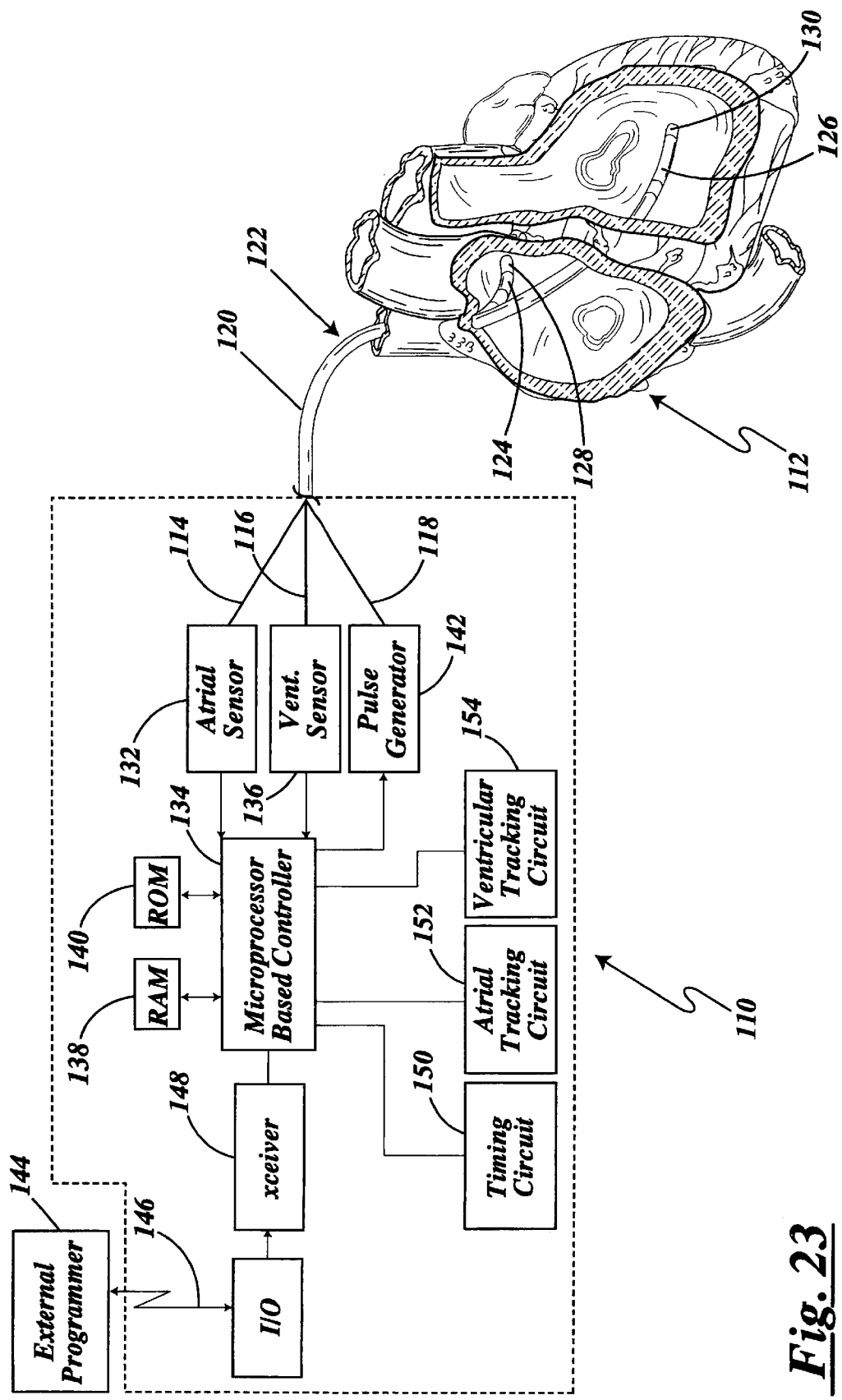
FIG. 23 is a block diagram showing the components of the ventricular tracking pacemaker of the present invention.

Referring next to FIG. 23, the preferred embodiment of the invention is shown generally in block diagram, wherein the cardiac stimulator or ventricular tracking pacemaker 110 (enclosed by a dotted line) operatively connects to a patient's heart 112 by electrical conductors 114, 116, and 118 embodied in a pacing lead 120 for atrial and ventricular dual chamber pacing. The first end of the pacing lead 122, inserted into the patient's heart 112, branches into an atrial branch 124 and a ventricular branch 126. The atrial branch 124 connects to a first set of stimulating and sensing electrodes 128 which are adapted to be disposed in the right atrium of the heart 112 and is arranged to sense the occurrence of P-wave activity relating to atrial events. The ventricular branch 126 connects to a second set of stimulating and sensing electrodes 130, which are adapted to be disposed in either the right or left ventricle of the heart. Those skilled in the art will appreciate that other pacing and/or sensing leads of suitable known construction may be coupled to the cardiac stimulator and disposed in the patient's heart.

The atrial branch 124 is connected by electrical conductor 114 to an atrial sense amplifier 132 which detects P-waves associated with atrial events. The resulting atrial event signal is fed to an input of a microprocessor-based controller 134. In a similar fashion, the ventricular. branch 126 is operatively coupled by-conductor 116. to a ventricular sense amplifier 136. The ventricular sense amplifier 136 functions to detect R-wave activity relating to ventricular depolarization. The signal representing the R-wave activity is then fed to an input of a microprocessor-based controller 134.

The microprocessor-based controller 134 is programmed to operate in any one of a plurality of known pacing modes and includes a ventricular tracking mode of the present invention. Also coupled to the microprocessor 134 is a timing circuit 150, atrial tracking circuit 152, and ventricular tracking circuit 154. The microprocessor 134 has both RAM (random access memory) 138, and ROM (read only memory) 140 for storing programs and data, which allows: the processing of the sensed signals, triggering the pulse generator 142, determining a sinus rate from the sensed signals, analyzing the sensed signals, and storing various information derived from the analysis. While FIG. 23 depicts a pacing/sensing lead in the right atrium and right ventricle, those skilled in cardiac rhythm management systems will appreciate that other leads of known construction may be positioned in other areas of the heart and coupled to corresponding amplifiers and the microprocessor-based controller.

The microprocessor 134 controls the cardiac stimulating pulses delivered by pulse generator 142 to one or both of the first and second stimulating electrodes 128 and 130 (depending upon the pacing mode selected). An external programmer 144 having a microprocessor and associated memory may transmit information in a conventional way through a telemetry link 146 and transmission receiver 148 of the cardiac stimulator's microprocessor. Using the programmer 144 and the telemetry link 146, operating parameter values for the pacemaker 110 can be delivered to it by a cardiologist for setting the cardiac cycle pacing parameter values to be utilized, including various timing intervals. Cardiac stimulating devices capable of telemetering various status information including selecting the pacing parameters and mode (determined by the physician) are commercially available from, for example, Cardiac Pacemakers, Inc., St. Paul, Minn.

Figure 24:
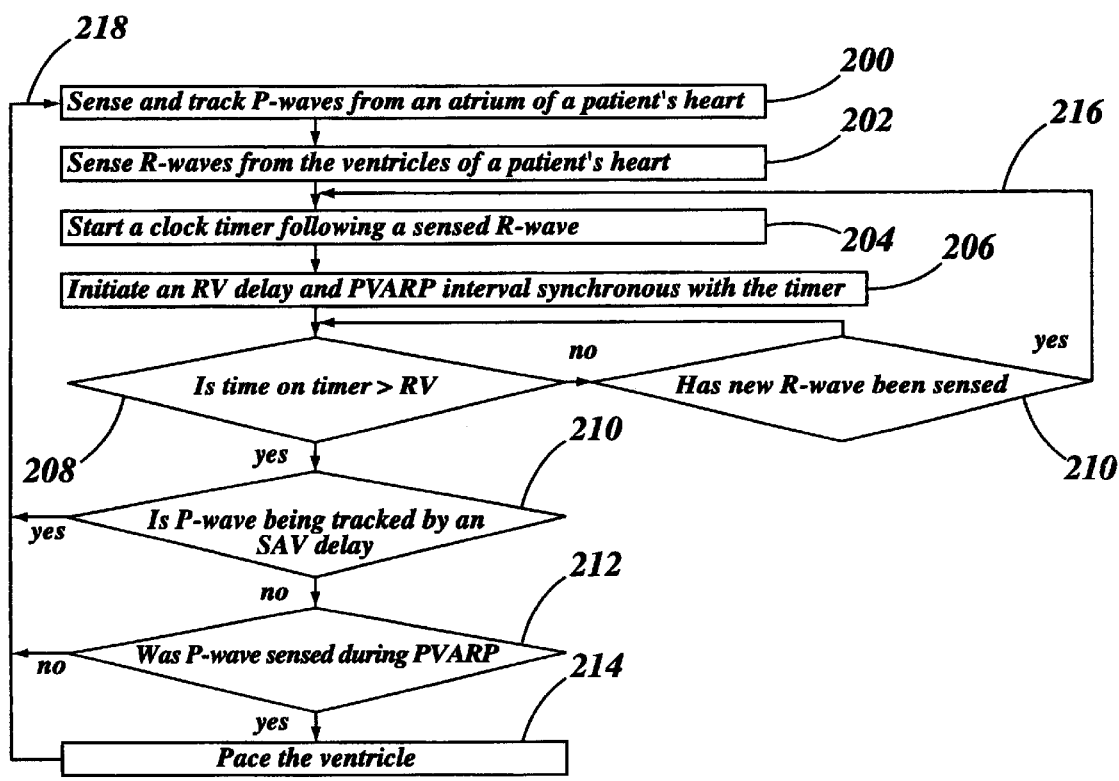
FIG. 24 is a flowchart showing the algorithm used by the ventricular tracking pacemaker of the present invention to track intrinsic conduction from the ventricle and accordingly pace the ventricle when rate priority timing is in effect.

FIG. 24 shows an algorithm that may be used by the ventricular tracking pacemaker of the present invention for rate priority ventricular tracking to track intrinsic conduction from the ventricle and accordingly pace the ventricle over a broader pacing range. Initially, a signal is transmitted through sensing lead 120 from the atrium of a patient's heart and P-waves from the signal are identified and tracked (see block 200). A signal is also transmitted through sensing lead 120 corresponding to events of the ventricle of a patient's heart and R-waves from the signal are identified (see block 202). The clock timer of the timing circuit 150, the RV delay interval and the PVARP interval are initialized in conjunction with the sensing of an R-wave (see blocks 204 and 206). Once the time on the clock timer exceeds the preset RV delay (see decision block 208) then the ventricle is paced at block 214 if: a P-wave is sensed during the PVARP interval, a sensed atrial to ventricular delay has not been started to track a P-wave sensed outside of PVARP (see decision blocks 210 and 212), and a second R-wave is not sensed during the RV delay interval (see decision block 210). If an R-wave is sensed during the RV delay interval, the timer is reset and the RV and PVARP intervals are re-initiated (see loop 216). If a P-wave is tracked by an SAV delay, the sensing and tracking is re-initiated (see loop 218). The ventricles will not be paced according to this algorithm, unless a P-wave is sensed during PVARP (see loop 218).

Figure 25:
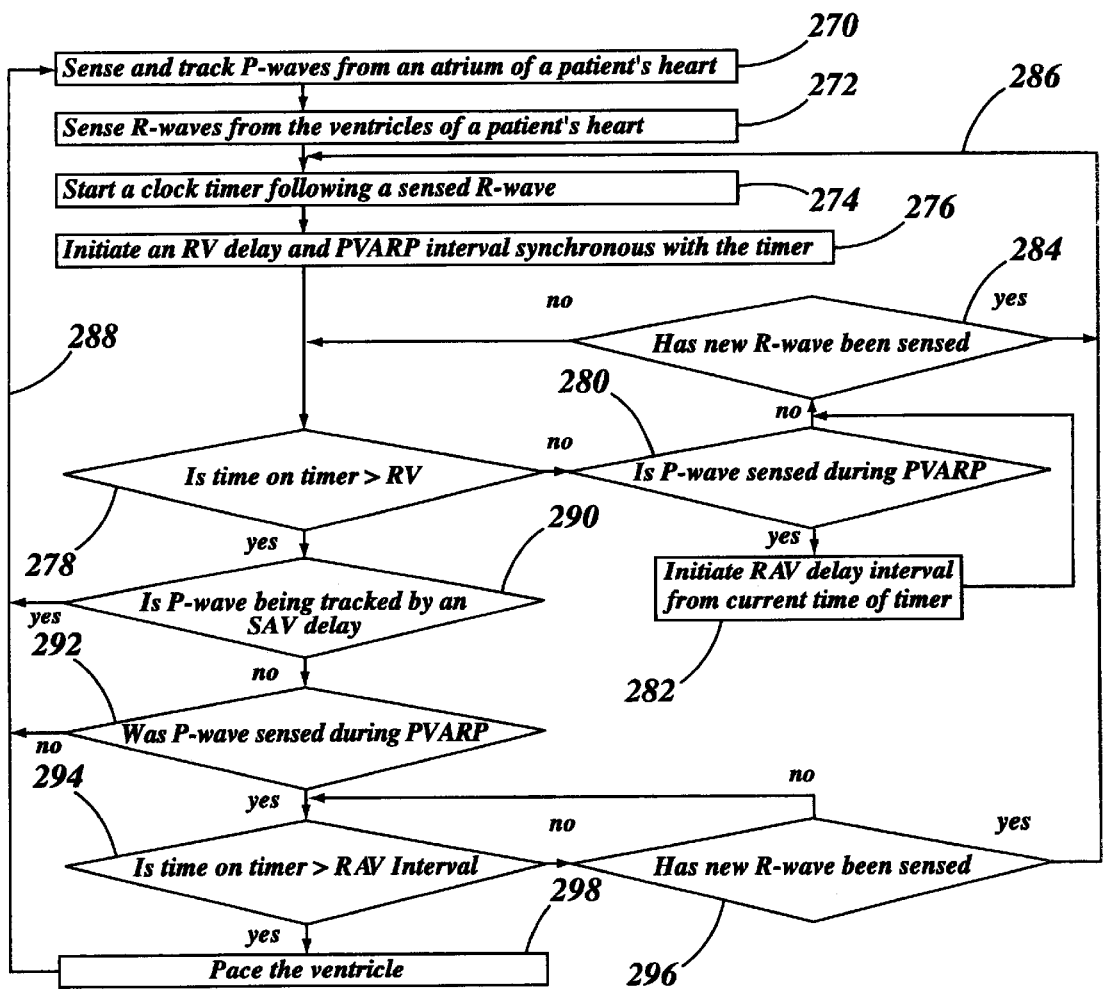
FIGS. 25 and 26 are flowcharts showing two algorithms that may be used by the ventricular tracking pacemaker of the present invention to track intrinsic conduction from the ventricle and accordingly pace the ventricle when delay priority ventricular tracking is in effect.
Figure 26:
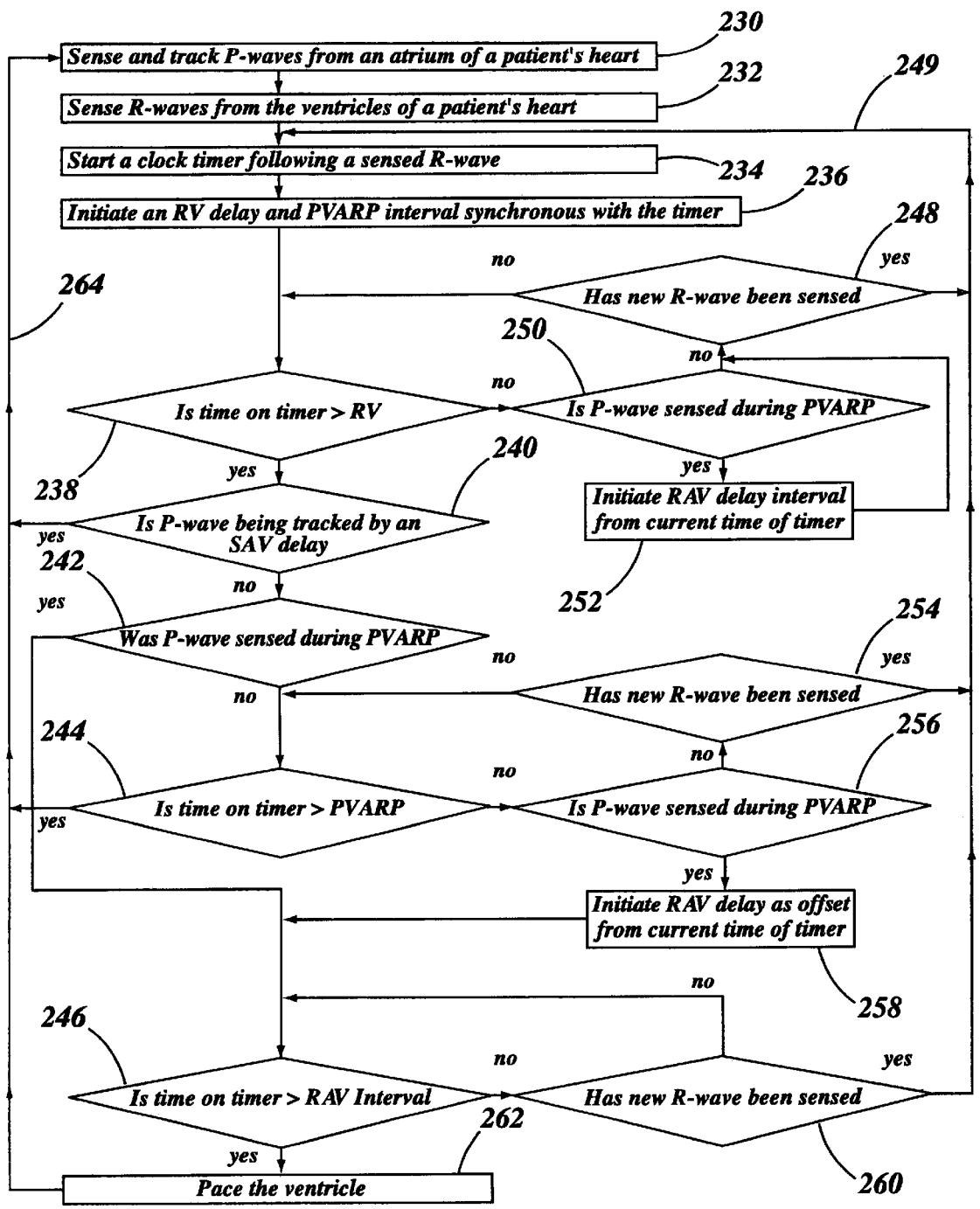

FIGS. 25 and 26 show algorithms that may be used by the ventricular pacemaker of the present invention for "delay priority" ventricular tracking. The algorithm shown in FIG. 25 is implemented when the RV interval is constrained to be greater than or equal to the PVARP. The algorithm shown in FIG. 26 is implemented when the RV interval is allowed to be less than the PVARP. Referring to FIG. 25, initially a signal is transmitted through sensing lead 120 from the atrium of a patient's heart and P-waves from the signal are identified and tracked (see block 270). A signal is also transmitted through sensing lead 120 corresponding to events of the ventricle of the patient's heart and R-waves from the signal are identified (see block 272). The clock timer of the timing circuit 150, the RV delay interval and the PVARP interval are initialized in conjunction with the sensing of an R-wave (see blocks 274 and 276). During a time not greater than the RV interval (see decision block 278) it is determined whether a P-wave is sensed during the PVARP interval (see decision block 280). If a P-wave is sensed during the PVARP interval, then a RAV interval is initiated from the current time (see block 282). Also during the time when the time of the clock timer is not greater than the RV interval, if an R-wave is sensed (as at decision block 284), then the clock timer is reset (see loop 286). When the time on the timer exceeds the RV interval, as at 278, then it is determined whether the P-wave is being tracked by an SAV delay (see decision block 290) and whether a P-wave has been sensed during PVARP (see decision block 292). If the P-wave is being tracked by an SAV delay or a P-wave has not been sensed during PVARP, then ventricular tracking is reset (see loop 288). If the P-wave is not being tracked by an SAV-delay and a P-wave has been sensed during PVARP, then the clock timer is compared to the RAV interval as at decision block 294. When the time of the clock timer exceeds the RAV interval, then the ventricle is paced as at block 298, unless an R-wave is sensed first (see block 296), which then resets the clock timer without pacing the ventricle and the algorithm is then repeated (see loop 286).

Referring now to FIG. 26, an algorithm is shown that may be used by the ventricular pacemaker of the present invention for "delay priority" ventricular tracking when the RV interval is allowed to be less than the PVARP. Initially, a signal is transmitted through sensing lead 120 from the atrium of a patient's heart and P-waves from the signal are identified and tracked (see block 230). A signal is also transmitted through sensing lead 120 corresponding to events of the ventricle of a patient's heart and R-waves from the signal are identified (see block 232). The clock timer of the timing circuit 150, the RV delay interval and the PVARP interval are initialized in conjunction with the sensing of an R-wave (see blocks 234 and 236). If the time on the timer is not greater than RV, and a P-wave is sensed during PVARP, then an RAV interval is initiated from the current time and it is then determined whether the time on the timer is greater than the RV as long as a new R-wave has not been sensed (see decision blocks 250, 252, 238 and 248).

Once the time on the clock timer exceeds the preset RV delay (see decision block 238) then it is determined whether the P-wave is being tracked by an SAV delay (see decision block 240). If the P-wave is being tracked by an SAV delay, then ventricular tracking is reset (see loop 264). If the P-wave is not being tracked by an SAV delay at decision block 240, then it is determined whether a P-wave has been sensed during PVARP (see decision block 242). If a P-wave is sensed during PVARP at 242 and the time is greater than the RAV interval (block 246), then the ventricle is paced at block 262. If a P-wave has not been sensed during PVARP at block 242, it is then determined whether the time is greater than PVARP (see decision block 244). When the time exceeds the PVARP as at 244, then ventricular pacing is reset (see loop 264) unless a P-wave is sensed during PVARP (see block 256). In that case, an RAV delay is initiated at the current time (see block 258), and after the time on the timer is greater than the RAV interval (see decision block 246), the ventricle is paced at 262 as long as a new R-wave has not been sensed (see decision block 260). If a new R-wave is sensed during the algorithm (see decision blocks 248, 254, and 260), then the clock timer is reset and the RV and PVARP delays are re-initiated (see loop 249).

Another algorithm that may be used by the ventricular tracking pacemaker of the present invention for delay priority ventricular tracking includes a pre-programmed modification of the conventional atrial tracking timing intervals after a sensed R-wave so that the atrial tracking rate is temporarily increased to the ventricular maximum tracking rate. When a pacing cycle follows a ventricular pace, the normal atrial tracking timing intervals are implemented by the pacemaker. However, when a pacing cycle follows a sensed R-wave, the atrial tracking timing intervals reset for the next cycle to the following: the atrial maximum tracking rate interval is set to equal the preset RV interval, the SAV interval is set to equal the preset RAV interval, and the PVARP interval is set to be less than the time of the RV interval minus the PR interval. With these reset timing intervals, a conventional atrial tracking algorithm is used to control ventricular pacing for the cycle (a conventional atrial tracking algorithm may include the following: when a P-wave is sensed outside of PVARP, the SAV interval is initiated and when it expires, the ventricle is paced unless the maximum tracking rate interval has not expired, in which case the ventricular pace is delayed until the end of the maximum tracking rate interval). After the cycle, the RV interval, SAV interval and PVARP intervals return to their preset intervals. Those skilled in the art will appreciate that this algorithm will produce the same pacing behavior as that described above in conjunction with FIG. 26.

It is recognized that the length of the RV delay and RAV intervals may be varied relative to other timing intervals of the pacemaker to control the ventricular tracking behavior of the ventricular tracking pacemaker. Further, the varied length of the RV delay and RAV intervals may also depend on features of a conventional atrial tracking pacemaker.

Figure 27:
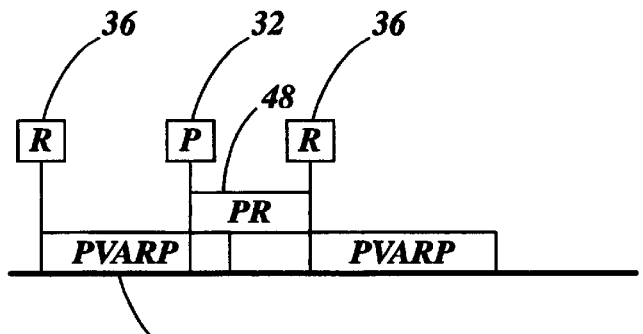
FIG. 27 is a plot showing a refractory P wave followed by a sensed R-wave (ref-P-R-wave) as a condition for tracking the sensed R-wave.

When tracking intrinsic ventricular electrical activity, it is important to be able to distinguish an R-wave that is naturally conducted from the atrium as opposed to an R-wave that is generated at an ectopic site, such as a premature ventricular contraction (PVC). This can be achieved by introducing an additional condition on the ventricular tracking algorithm, which is to track intrinsic conduction transmitted from a ventricle only when intrinsic conduction of an atrium is sensed before the end of the preceding PVARP timing interval. This "ref-P-R-wave" pattern-to be tracked is shown in FIG. 27. The R-wave 36 starts a PVARP 40 and a P-wave 32 is sensed before the end of the PVARP and an intrinsically conducted R-wave 36 is sensed after the intrinsic AV conduction delay (PR) 48 and tracked in the manner previously described.

Figure 28:
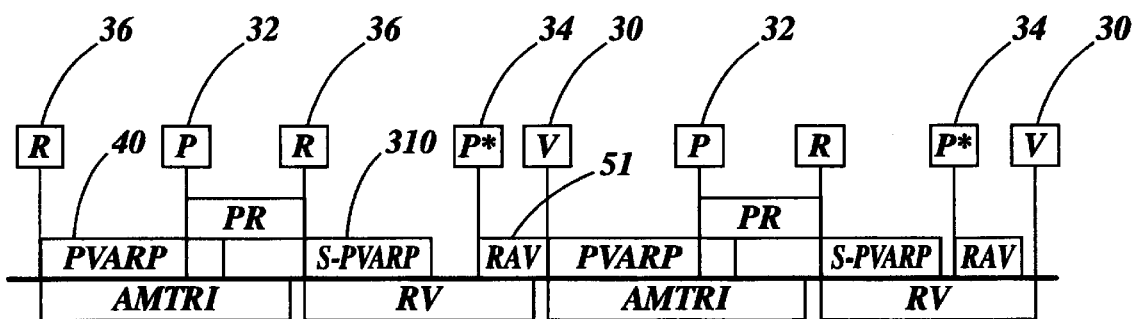
FIG. 28 is a plot showing the delay priority ventricular tracking algorithm with the S-PVARP method combined with the RV interval.

FIG. 28 illustrates another embodiment for the ventricular tracking protocol that may be used by the ventricular tracking pacemaker of the present invention for delay priority ventricular tracking. The protocol includes a pre-programmed modification of the conventional atrial tracking timing intervals after a sensed R-wave or after a ref-P-R-wave pattern so that the atrial tracking rate is temporarily increased to the ventricular maximum tracking rate. This is achieved partly by resetting the PVARP interval to a shorter preset interval called the S-PVARP interval (ranging between 0 and RV−PR), as follows: when a pacing cycle follows a ventricular pace, the normal atrial tracking timing intervals are implemented by the pacemaker. However, when a pacing cycle follows a sensed R-wave or follows a ref-P-R wave pattern, the atrial tracking timing intervals reset for the next cycle to the following: the atrial maximum tracking rate interval is set to equal the RV interval and the PVARP interval is set to equal the S-PVARP interval, and the SAV interval is set equal to the preset RAV interval. The preset RAV interval can be equal to the SAV interval, in which case the normal SAV interval is not reset. With these reset timing intervals, a conventional atrial tracking algorithm is used to control ventricular pacing for the cycle (a conventional atrial tracking algorithm may include the following: when a P-wave is sensed outside of PVARP, the SAV interval is initiated, and when it expires, the ventricle is paced unless the maximum tracking rate interval has not expired, in which case the ventricular pace is delayed until the end to the maximum tracking rate interval). After the ventricular tracking cycle, the atrial maximum tracking rate, PVARP, and SAV intervals return to the normal atrial tracking timing intervals.

As shown in FIG. 28, the R-wave 36 starts a normal PVARP 40 and a P-wave 32 is sensed before the end of the PVARP 40. An intrinsically conducted R-wave 36 is then sensed and tracked as follows: the S-PVARP interval 310 and the RV interval 42 are substituted for the normal PVARP 40 and AMTRI 50. When the next P-wave 32 is sensed after the end of S-PVARP 310, it starts the atrio-ventricular pacing delay (AV delay), which is preset to the RAV 51. When this interval expires, the ventricle is paced at 30, because the RV interval 42 has also expired. The next cycle is a normal atrial tracking cycle. The last cycle shown is another ventricular tracking cycle, which shows an example of the ventricular pace 30 being delayed until the end of the RV interval 42 when the RAV 51. interval expires first. When the P-wave is sensed during S-PVARP 310 it does not start an RAV interval.

Figure 29:
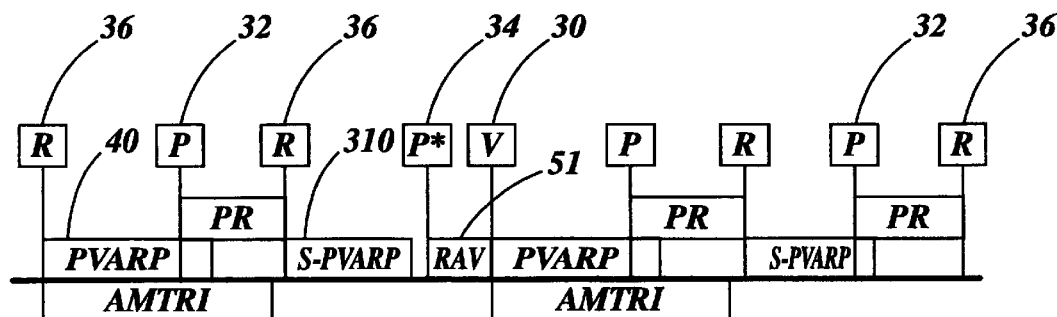
FIG. 29 is a plot showing the delay priority ventricular tracking algorithm with the S-PVARP method alone.

Without limitation, in the preferred embodiment the S-PVARP 310 can be set from a minimum of zero milliseconds up to a maximum of the normal PVARP (e.g., 500 milliseconds). When the S-PVARP 310 is used as the method of ventricular tracking, the RV interval 42 can be set from a minimum of the sum of the S-PVARP and RAV intervals (S-PVARP+RAP) up to a maximum of the normal atrial maximum tracking rate interval (e.g., 1200 milliseconds). When the RV interval is equal to the sum of the S-PVAPP and RAV intervals, the delay priority ventricular tracking algorithm can be simplified as follows. When a pacing cycle follows a ventricular pace, the normal atrial tracking timing intervals are implemented by the pacemaker. However, as shown in FIG. 29 when a pacing cycle follows a sensed R-wave or follows a ref-P-R-wave pattern, the PVARP interval is set to equal the S-PVARP interval; the SAV interval is set equal to the preset RAV interval if these two intervals are different, and the atrial maximum tracking rate interval is ignored. With these reset timing intervals, a conventional atrial tracking algorithm is used to control ventricular pacing for the ventricular tracking cycle, except the normal atrial maximum tracking rate limit is ignored. After the ventricular tracking cycle, the PVARP and SAV intervals return to the normal atrial tracking timing intervals, and the normal atrial maximum tracking rate limit is enforced. This algorithm is represented in FIG. 29.

As shown in FIG. 29 the R-wave 36 starts a normal PVARP 40 and a P-wave 32 is sensed before the end of the PVARP 40. An intrinsically conducted R-wave 36 is then sensed and tracked as follows: the S-PVARP interval 310 is substituted for the normal PVARP 40 and the AMTRI 50 is ignored. When the P-wave 32 is sensed after the end of S-PVARP 310, it starts the AV delay, which is preset to the RAV 51. When this interval expires, the ventricle is paced. The next cycle shown is a normal atrial tracking cycle. The last cycle is another ventricular tracking cycle, which shows an example of the P-wave 32 being sensed during S-PVARP 310 and thus not starting the RAV interval 51 so ventricular pacing does not occur and the intrinsically conducted R-wave 36 is sensed.

Figure 30:
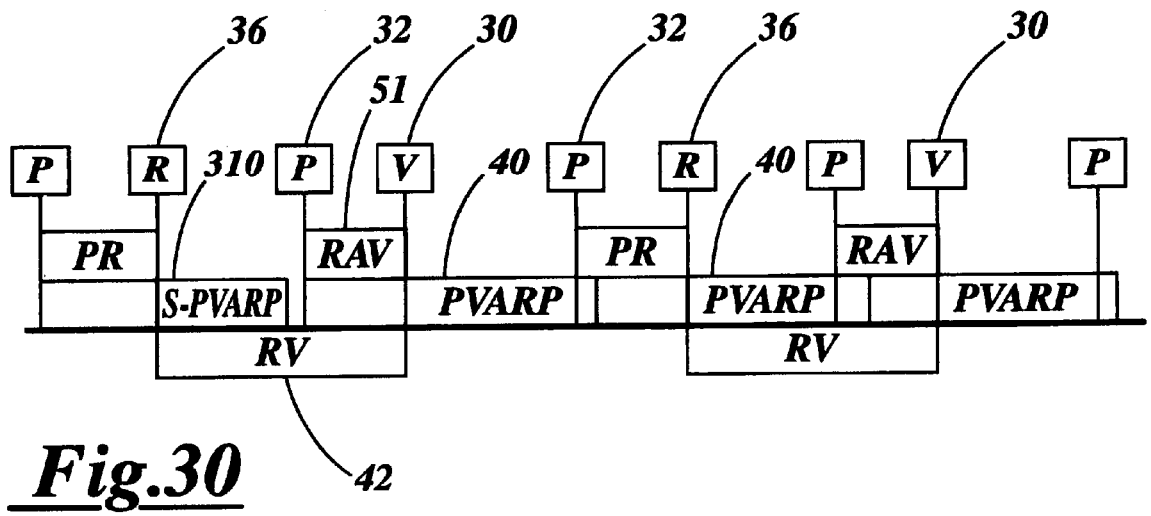
FIG. 30 is a plot showing ventricular oscillation occurring when there is 2:1 ventricular tracking when the PP interval is less than the MHI.

Those skilled in the art will appreciate that the ventricular tracking timing intervals of the present invention may be set to avoid ventricular rate oscillation. One of the consequences of the ventricular tracking protocol described above is that the ventricular rate can oscillate for some settings of the RV and other ventricular tracking intervals. As shown in FIG. 30, ventricular rate oscillation occurs when there is 2:1 ventricular tracking when the PP interval is less than the MHI (as defined below). Ventricular tracking is initiated at the R-wave 36 which starts the RV interval 42 and the S-PVARP interval 310 after which a P-wave 32 will initiate the RAV interval 51. A ventricular pace 30 occurs at the end of the RAV interval (or alternatively at the end of the RV interval in rate priority ventricular tracking) and starts a normal PVARP interval that blocks the sensing of the next P-wave 32. Thus a naturally conducted R-wave 36 occurs and triggers another cycle of ventricular tracking that ends with a ventricular pace 30. This pattern will continue until the PP interval becomes greater than MHI. The present invention can avoid rate oscillation by appropriately selecting preset atrial tracking and ventricular tracking intervals as described below.

Figure 31:
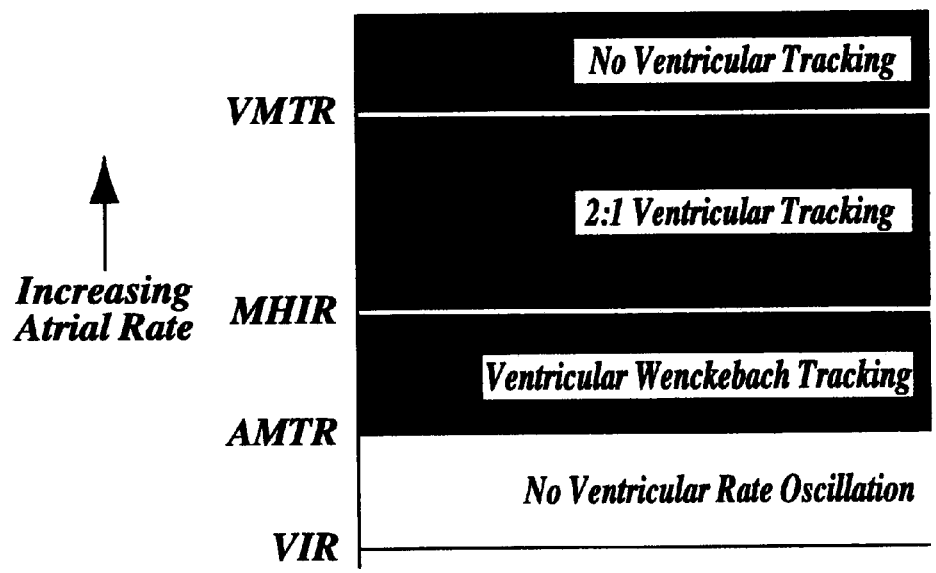
FIG. 31 is a graph showing the distribution of ventricular rate oscillation when the AMTR is less than MHIR.
Figure 32:
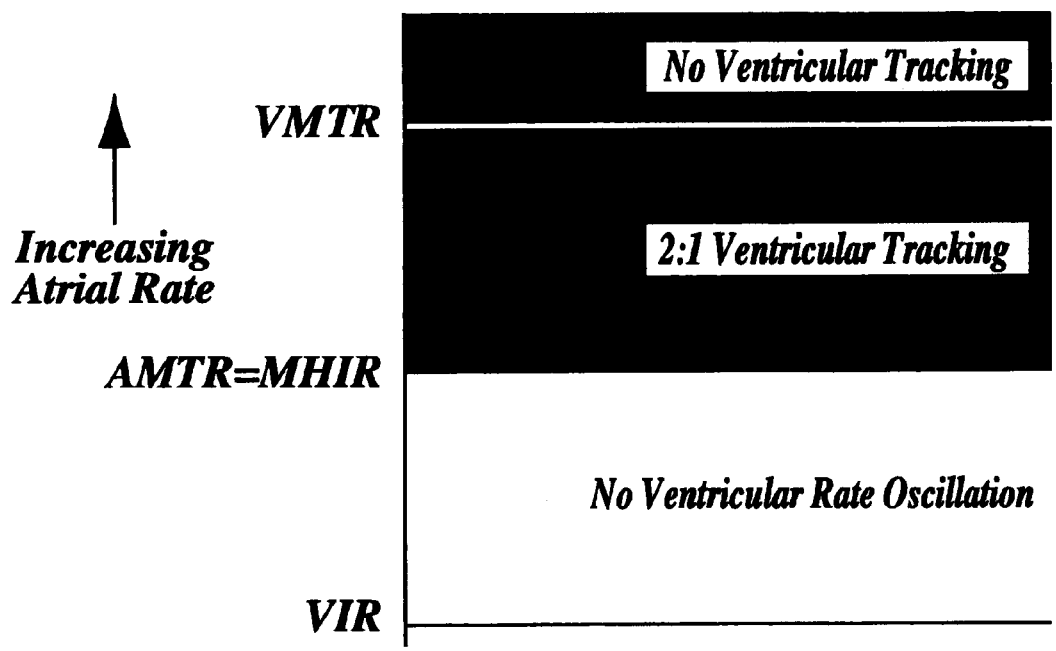
FIG. 32 is a graph showing the distribution of ventricular rate oscillation when AMTR is equal to MHIR.
Figure 33:
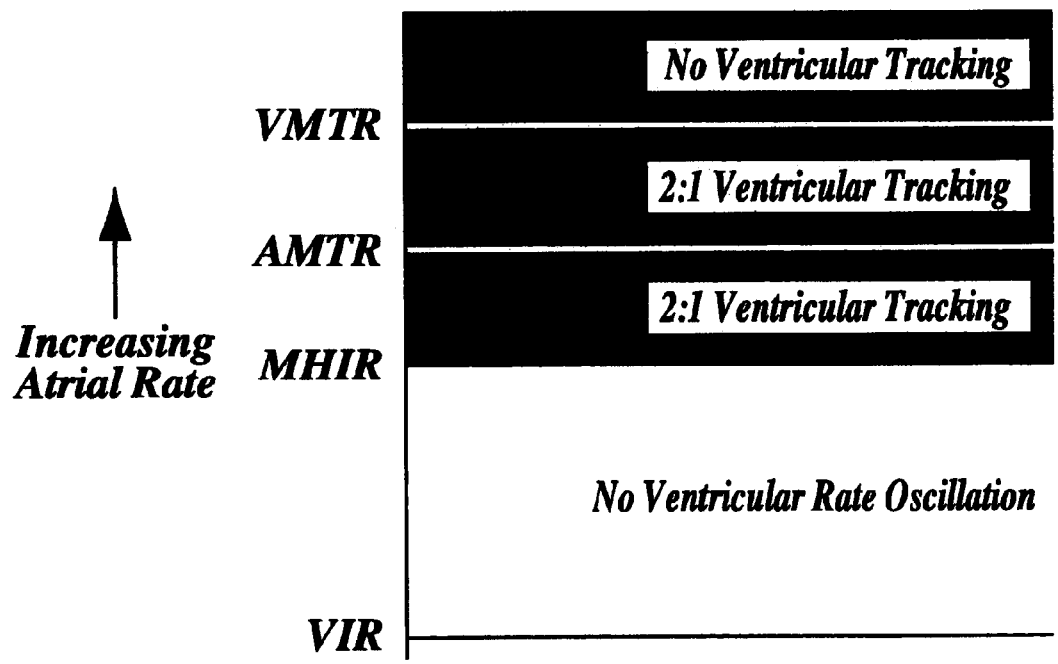
FIG. 33 is a graph showing the distribution of ventricular rate oscillation when the AMTR is greater than MHIR.

Referring now to FIGS. 31–33, the graphs illustrate that ventricular rate oscillation will occur when the atrial rate interval (PP interval) is less than the middle hysteresis interval (MHI) where MHI is defined as follows: MHI=(RV+PVARP+PR)/2. PR is the intrinsic atrio-ventricular conduction delay. The rate oscillation occurs because the algorithm oscillates between ventricular tracking and normal atrial tracking. An example of 2:1 tracking oscillation is shown in FIG. 30 when the PP interval is less than the MHI. The ventricular maximum tracking rate (VMTR) is the rate equivalent to the RV interval, and the ventricular inhibition rate (VIR) is the rate equivalent to the sum of PVARP and PR intervals (PVARP+PR). Also, there is no ventricular tracking when atrial rates are greater than the VMTR. The relationship of the MHI to the atrial maximum tracking rate (AMTR), VMTR, and VIR is shown in FIGS. 31–33 where MHIR is the rate equivalent to the MHI. When the AMTR is below the MHIR (FIG. 31), there is no ventricular rate oscillation when atrial rates are less than AMTR, but there is ventricular Wenckebach tracking or 2:1 ventricular tracking when atrial rates are above AMTR. When the AMTR is equal to the MHIR (FIG. 32), there is no ventricular rate oscillation when atrial rates are less than AMTR, but there is 2:1 ventricular tracking when atrial rates are greater than AMTR. Finally when the AMTR is above the MHIR (FIG. 33), there is 2:1 ventricular tracking for atrial rates above the AMTR and between the AMTR and the MHIR. Thus, ventricular rate oscillation associated with the ventricular tracking algorithm can be avoided for all atrial rates below the atrial maximum tracking rate by programming the RV, PVARP, and AMTR intervals in accordance with AMTRI≧MHI.

In another embodiment of the ventricular tracking protocol, ventricular rate oscillation is reduced by delaying the activation of ventricular tracking for some preset number of cardiac cycles either before or after an intrinsic ventricular conduction is sensed. For example, let n be a counter initialized to zero at the end of a ventricular tracking cycle that is incremented by one each time an R-wave or a ref-P-R-wave pattern is sensed. Let m be a counter initialized to one at the end of a ventricular tracking cycle that is incremented by one at the end of each subsequent cardiac cycle that is not a ventricular tracking cycle. Then the ventricular tracking protocol of this invention includes a comparator and preset parameters N and M such that the ventricular tracking algorithm will not be applied until the comparator determines at the start of a cardiac cycle that n>N and m>M. Without limitation, a possible range of N or M is 0 to 500. This delayed activation method can be applied to all embodiments of the ventricular tracking protocol, including S-PVARP ventricular tracking and multicycle ventricular tracking.

Figure 34:
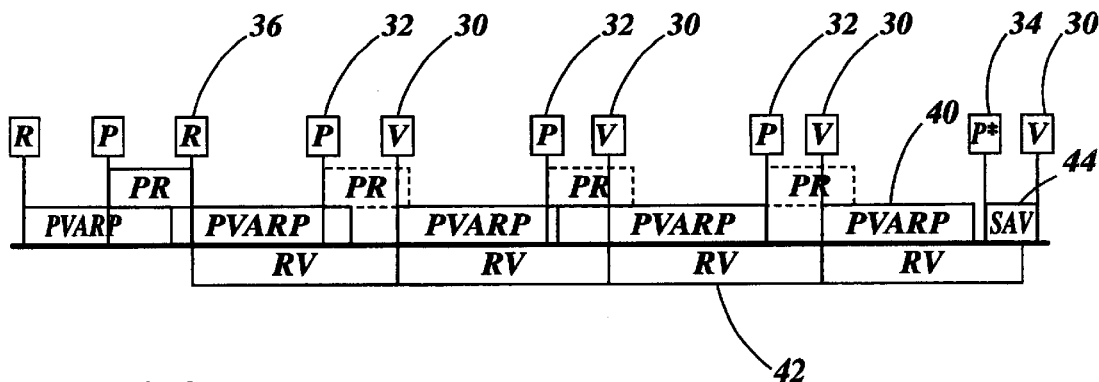
FIG. 34 is a plot showing a rate priority multicycle ventricular tracking algorithm with RV set equal to the AMTR interval.

In yet another embodiment of the ventricular tracking protocol of the present invention, referred to herein as multicycle ventricular tracking, the protocol avoids ventricular rate oscillation for atrial rates below the AMTR even when the AMTR is greater than the MIHR (see FIG. 33). This embodiment may be useful when the AMTR must be programmed above the MIH rate or when ventricular pacing above atrial maximum tracking rate is not permitted, that is, when the RV interval must be set equal to the AMTR interval. The multicycle algorithm repetitively applies rate priority or delay priority ventricular tracking to consecutive cardiac cycles starting when an R-wave sense or the ref-P-R-wave pattern occurs while the atrial rate is less than AMTR. Ventricular tracking continues on subsequent cycles until the atrial rate becomes higher than the AMTR or until a ventricular pace caused by expiration of the SAV or RAV interval occurs. Then the normal atrial tracking intervals are restored. In this embodiment, the ventricular tracking RV interval is set equal to or less than the AMTR interval. When the RV interval is set equal to the AMTR interval, the ventricular pacing rate will never exceed the AMTR, which may be important for some applications. FIG. 34 shows rate priority multicycle ventricular tracking and FIG. 35 shows delay priority multicycle ventricular tracking.

As shown in FIG. 34, multicycle ventricular tracking is triggered at the R-wave 36 which starts the RV interval. The next sensed P-wave 32 is sensed during PVARP so a ventricular pace 30 is generated at the end of the RV interval 42. Since the PP interval is still longer than the AMTR interval and pacing did not occur at the end of a SAV interval 44, ventricular tracking is applied-to the next cycle. In this cycle, the P-wave 32 again is sensed during PVARP and a ventricular pace is generated at the end of the RV interval 42 and likewise for the P-wave 32 and ventricular pace 30 in the next cycle. During the last cycle shown, the P-wave 32 is sensed after the end of PVARP 40 and is tracked by normal atrial tracking so that the ventricular pace 30 occurs at the end of the SAV interval 44 and multicycle ventricular tracking is terminated and normal atrial tracking is restored for subsequent cycles.

Figure 35:
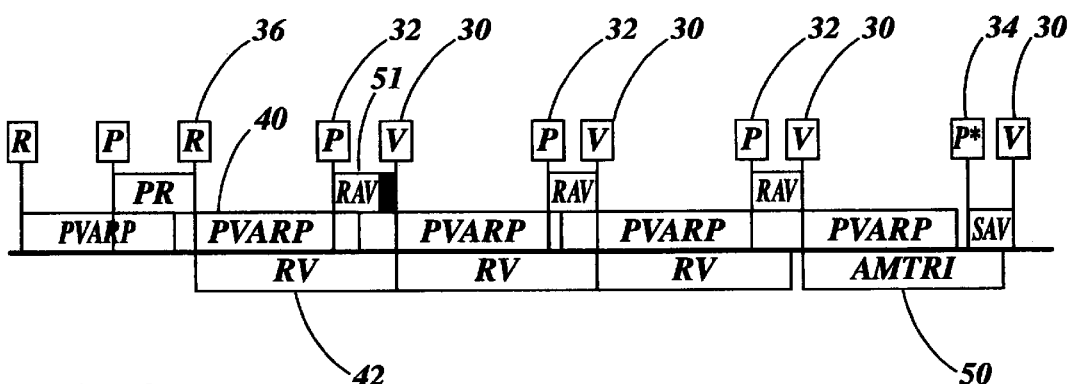
FIG. 35 is a plot showing a delay priority multicycle ventricular tracking algorithm with RV set less than the AMTR interval.

As shown in FIG. 35 the multicycle ventricular tracking is triggered at R-wave 36 which starts the RV interval 42. The next P-wave 32 is sensed during PVARP 40 so the RAV interval 51 is initiated but terminates before the RV interval 42 expires, thereby delaying a ventricular pace 30 until the end of the RV interval 42. Since the PP interval is still longer than the AMTR interval (not shown for this cycle) and pacing did not occur at the end of a RAV interval 51, ventricular tracking is applied to the next cycle. In this cycle, the P-wave 32 again is sensed during PVARP 40 which starts the RAV interval 51. The RAV interval ends just before the RV interval 42 expires so a ventricular pace 30 occurs at the end of the RV interval, and ventricular tracking is applied to the next cycle. During this cycle, the P-wave 32, is sensed during PVAPP and initiates the RAV interval, which ends after the RV interval expires so a ventricular pace occurs at the end of the RAV interval 51. This terminates multicycle ventricular tracking and normal atrial tracking intervals are restored for the last cycle.

In one embodiment of the multicycle ventricular tracking, the atrial rate may be determined from the timing of consecutive sensed P-waves, or it can be determined from intrinsically conducted sensed R-waves. At the start of each new cardiac cycle, this atrial rate is compared to the AMTR. If it is less than the AMTR by a preset delta, $d_1$, then the ventricular tracking protocol is applied when an R-wave or a ref-P-R-wave pattern is detected. One possible rate range of $d_1$ is 0 to 10 bpm or one possible interval range of $d_1$ is 0 to 50 milliseconds.

Figure 36:
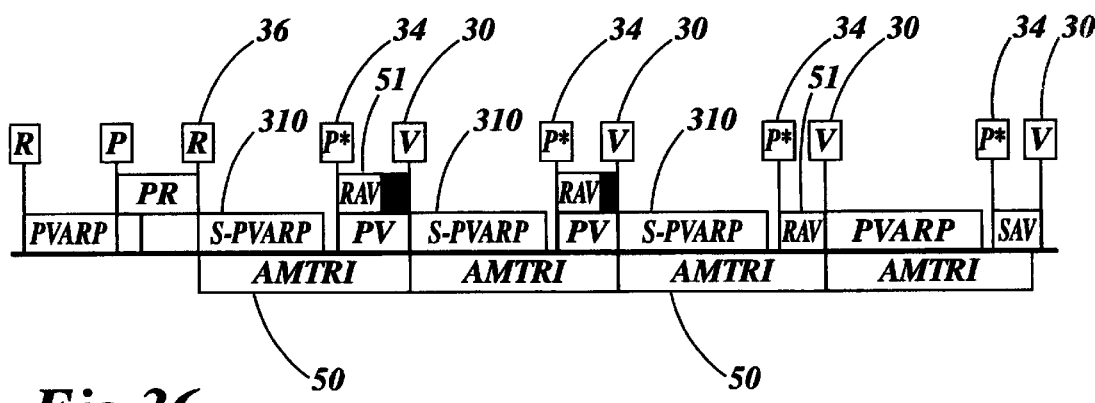
FIG. 36 is a plot showing a multicycle ventricular tracking algorithm using a dynamic S-PVARP.
Figure 37:
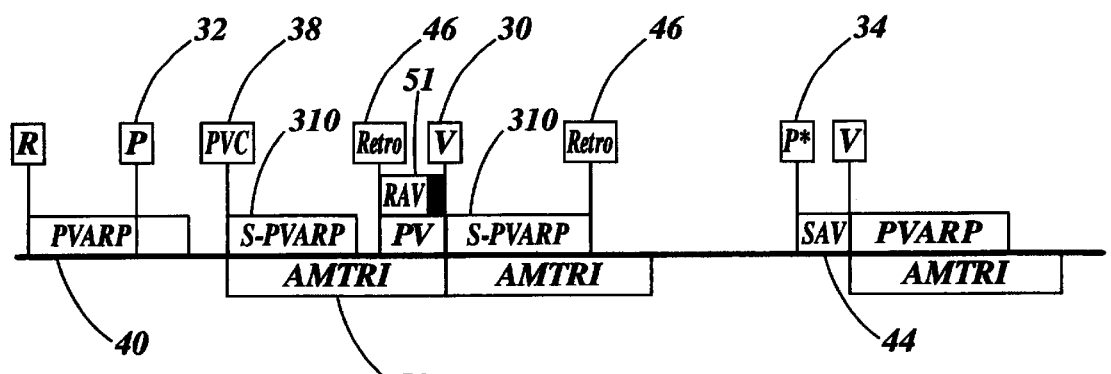
FIG. 37 is a plot showing a multicycle ventricular tracking algorithm avoiding PMT due to retrograde conduction.

Alternatively, the S-PVARP method of ventricular tracking is used and the S-PVARP is set dynamically so that the atrial rate does not have to be determined. In this embodiment, the RV interval is not used, since the AMTR interval normally programmed for atrial tracking is sufficient. In this embodiment, when a ref-P-R-wave pattern is detected after a period of ventricular pacing, the PVARP of the next cycle is set equal to the initial S-PVARP. The initial S-PVARP is either set to a preset value such that S-PVARP≧ATRI-PR or it is set dynamically according to the following equation: S-PVARP=AMTRI-PR-$d_2$, where PR is the time delay recorded between the sensed P-wave and the sensed R-wave of the previous cardiac cycle and $d_2$ is a timing accuracy offset. One possible interval range of $d_2$ is 0 to 50 milliseconds. Then on each subsequent cardiac cycle when the R-wave or ref-P-R-wave pattern is detected, the PVARP is set equal to a dynamic S-PVARP interval, which is set according to the following equation: S-PVARP= AMTRI-PV-$d_3$ where PV is the time delay recorded between the P-wave and the ventricular pace of the previous cardiac cycle and $d_3$ is a timing accuracy offset. One possible interval range of $d_3$ is −50 to 50 milliseconds. This embodiment of multicycle ventricular tracking is shown in FIG. 36. FIG. 36 shows a successful return to normal atrial tracking after three S-PVARP cycles. Negative values of $d_3$ help prevent pacemaker-mediated tachycardia (PMT) as illustrated in FIG. 37. The algorithm behavior for atrial rates crossing above and below AMTR is illustrated in FIG. 38 and 39, respectively.

FIG. 36 shows multicycle ventricular tracking using a dynamic S-PVARP. Ventricular tracking is applied at ref-P-R-wave 36 and followed by setting PVARP to S-PVARP so that the P-wave 32 is tracked and initiates an RAV interval 51 that ends before AMTRI expires so ventricular pacing 30 is delayed until the AMTRI expires. This situation triggers another ventricular tracking cycle with the S-PVARP 310 set equal to AMTRI-PV of the preceding cycle (when $d_3$=0). During this cycle, ventricular pacing 30 is again delayed by the AMTRI 50, which triggers another ventricular tracking cycle. The S-PVARP 310 is set dynamically but on this cycle ventricular pacing 30 occurs at the end of the RAV interval 51. Because ventricular pacing was not delayed by the AMTRI, normal atrial tracking intervals are restored for the last cycle.

FIG. 37 shows the multicycle ventricular tracking avoiding PMT due to retrograde conduction. The P-wave 32 did not conduct to the ventricle and a PVC 38 occurs after PVARP, which triggers ventricular tracking to change PVARP 40 to S-PVARP 310. However, the PVC 38 causes a retrograde P-wave 46 that starts the RAV interval 51 that times out before the end of AMTRI 50 so that the ventricular pace 30 occurs at the end of AMTRI 50. This situation triggers another ventricular tracking cycle, and PVARP 40 is changed to S-PVARP 310, but this S-PVARP is set to AMTRI-PV-$d_3$ of the previous cycle, which equals the retrograde conduction time or is greater than the retrograde conduction time when $d_3$ is negative so that the next retrograde P-wave 46 falls into the S-PVARP 310 and does not start an RAV interval. The next P-wave 32 is naturally conducted and tracked by normal atrial tracking intervals.

Figure 38:
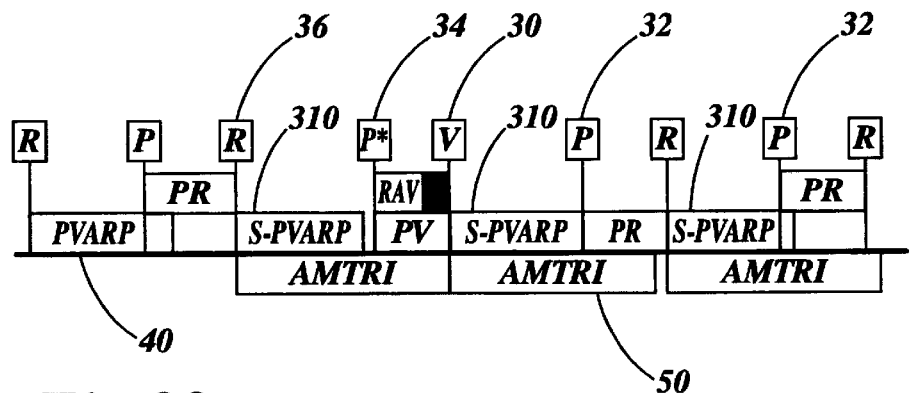
FIG. 38 is a plot showing a multicycle ventricular algorithm when the atrial rate rises from below AMTR to above AMTR.
Figure 39:
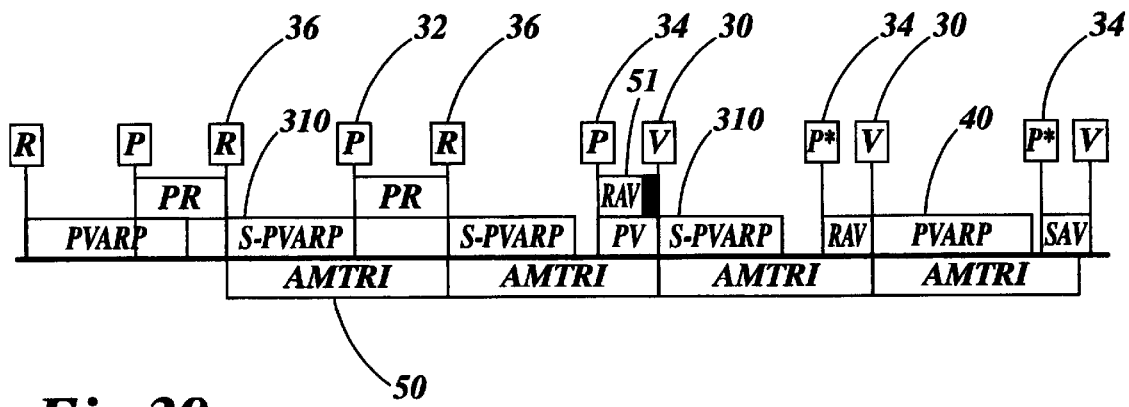
FIG. 39 is a plot showing a multicycle ventricular tracking algorithm when the atrial rate falls from above AMTR to below AMTR.

FIG. 38 illustrates multicycle ventricular tracking when the atrial rate rises from below AMTR to above AMTR. Multicycle ventricular tracking is triggered at the ref-P-R-wave 36 and changes PVARP to S-PVARP 310, which allows the next P-wave 32 to start the RAV interval, which terminates before the end of AMTRI so the ventricular pace is delayed to the end of AMTRI 50. This situation triggers another ventricular tracking cycle, but in this cycle, the P-wave 32 is sensed before the end of S-PVARP, because the PP interval equals the AMTRI. In the last cycle shown, the S-PVARP 310 is set to AMTRI-PR (when $d_3$=0) and the PP interval is less than AMTRI. This setting of S-PVARP will occur on every subsequent cycle as long as the PP interval remains less than AMTRI.

FIG. 39 illustrates multicycle ventricular tracking when the atrial rate falls from above AMTR to below AMTR. The multicycle ventricular tracking is triggered at the ref-P-R-wave 36 and the next P-wave 32 is sensed during S-PVARP 310 because the PP interval is equal to AMTRI. However, after the next naturally conducted R-wave 36 the next P-wave 32 occurs at a PP interval longer than AMTRI so that it is sensed after the end of S-PVARP and starts the RAV interval, which ends before AMTRI so that the ventricular pace is delayed until the end of the AMTRI 50. This situation triggers another ventricular tracking cycle. In this cycle, the P-waves occurs at a PP interval longer than AMTRI so a ventricular pace 30 occurs that is not limited by AMTRI. Then on the last cycle normal atrial tracking intervals are restored. In another embodiment of multicycle ventricular tracking, the S-PVARP method of ventricular tracking is combined with substitution of the RV interval for the AMTR interval on each ventricular tracking cycle. Since the RV interval can be less than the AMTR interval, this embodiment will restore normal atrial tracking intervals faster than when the AMTR interval is not changed. This embodiment is the same as described previously corresponding to FIGS. 36–39, except that each time the S-PVARP is substituted for the PVARP, the RV interval is also substituted for the AMTRI. This substitution is illustrated in FIG. 40.

Figure 40:
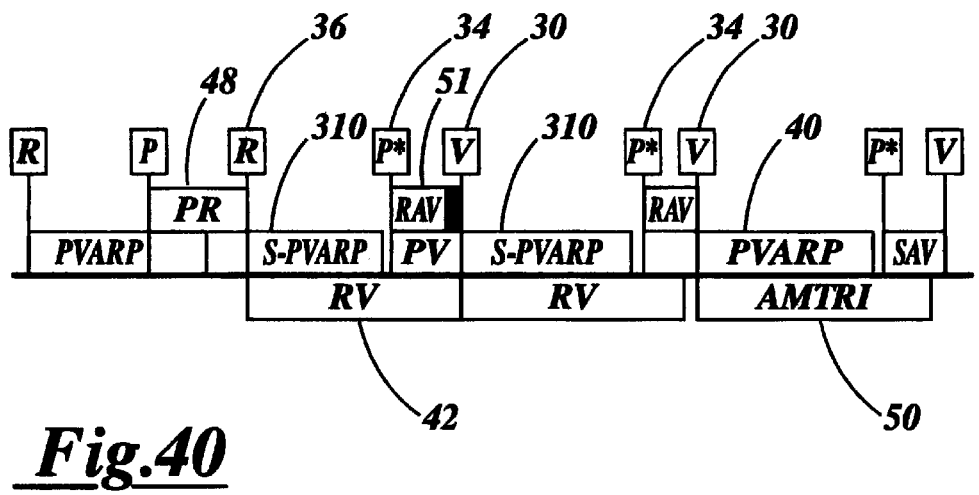
FIG. 40 is a plot showing a multicycle ventricular tracking algorithm using dynamic S-PVARP and the RV interval.

FIG. 40 illustrates multicycle ventricular tracking using dynamically the S-PVARP and the RV interval. Ventricular tracking is applied at ref-P-R-wave 36 which is followed by setting PVARP to S-PVARP 310 and AMTRI to RV 42. The next P-wave 32 is sensed after the end of S-PVARP so it starts the RAV interval 51, which ends before the RV interval expires so the ventricular pace 30 occurs at the-end of the RV interval. This situation triggers another ventricular tracking cycle. During the next cycle, the next P-wave 32 is sensed after S-PVARP and starts the RAV interval that ends after the RV interval expires so the ventricular pace occurs at the end of the RAV interval. This situation terminates the ventricular tracking so that normal atrial tracking intervals are restored for the last cycle.

In yet another embodiment of Delay Priority Ventricular Tracking, ventricular tracking includes a pre-programmed modification of the conventional atrial tracking VA timing interval that occurs after a ref-P-R wave pattern so that the atrial pacing rate is temporarily increased to be above the intrinsic atrial rate. The pre-programmed modified VA interval shall be called the S-VA interval. For conventional atrial tracking modes, the VA timing interval is initiated when an intrinsic conduction from the ventricle is sensed or when the ventricle is paced. The VA interval continues until it expires, unless it is terminated when an intrinsic conduction from the atrium is sensed after the PVARP interval has expired or an intrinsic conduction from the ventricle is sensed. If an intrinsic atrial conduction is sensed after the PVARP interval, the SAV interval is initiated, and when it expires the ventricle is paced unless an intrinsic R-wave is sensed before the end of the SAV interval. Also, the ventricular pace might be delayed to prevent pacing faster than the atrial maximum tracking rate (AMTR). If an intrinsic atrial conduction is not sensed after the end of the PVARP interval and before the end of the VA interval, the atrium is paced when the VA interval expires, and the paced AV delay (PAV) interval is initiated. When the PAV interval expires, the ventricle is paced, unless an intrinsic R-wave is sensed before the end of the PAV.

For ventricular tracking of the present invention, the normal VA interval is set equal to the S-VA interval and is initiated when a sensed R-wave or a ref-P-R-wave pattern is detected. Then, when the S-VA interval expires, the atrium is paced and the normal PAV interval is initiated, unless an intrinsic atrial sense occurs after the end of the PVARP interval and before the end of the S-VA interval, in which case the VA interval is terminated and the normal SAV interval is initiated. The ventricular tracking algorithm with the S-VA interval is illustrated in FIGS. 41–43.

Figure 41:
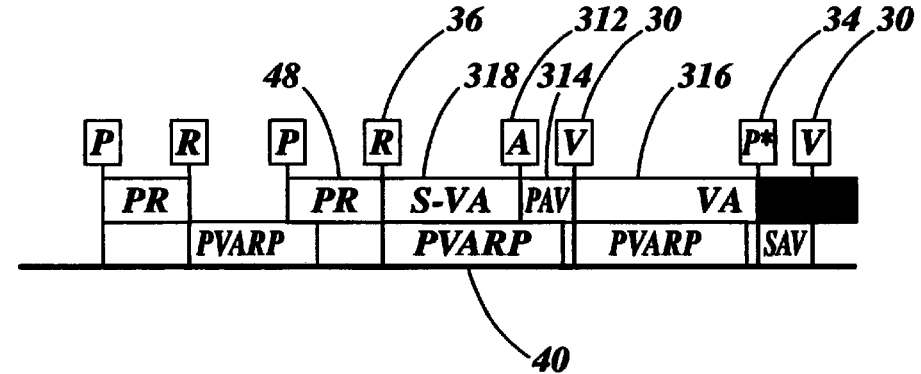
FIG. 41 is a plot showing ventricular tracking with the S-VA interval.

FIG. 41 illustrates ventricular tracking utilizing the S-VA interval. Ventricular tracking is triggered by the R-wave sense 36 which starts the S-VA interval 31 8. When the S-VA interval 318 expires, the atrium is paced at 312 and a PAV interval 314 is initiated, and the ventricle is paced when the PAV interval 314 ends. Normal atrial tracking intervals are restored on the next cycle, where a P-wave 32 is sensed before the end of the VA interval 316 (indicated by shaded region).

Figure 42:
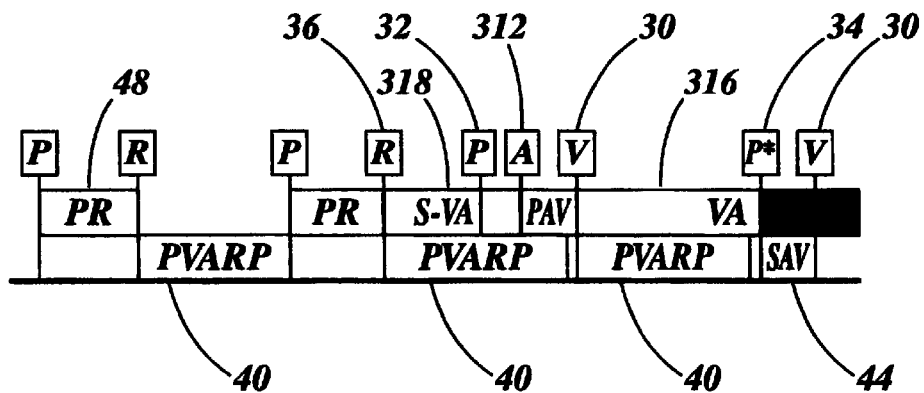
FIG. 42 is a plot showing ventricular tracking with the S-VA interval when a P-wave is sensed during the S-VA interval and before the end of PVARP.

FIG. 42 illustrates ventricular tracking utilizing an S-VA interval when a P-wave is sensed during the S-VA interval and before the end of PVARP. Ventricular tracking is triggered at the R-wave sense 36 which starts the S-VA interval 318. A P-wave 32 sense occurs before the end of the S-VA interval 318 and before the end of the PVARP interval 40 so it is ignored and the atrium is paced at the end of the S-VA interval 312. The rest of the cycle follows the sequence described for FIG. 41.

Figure 43:
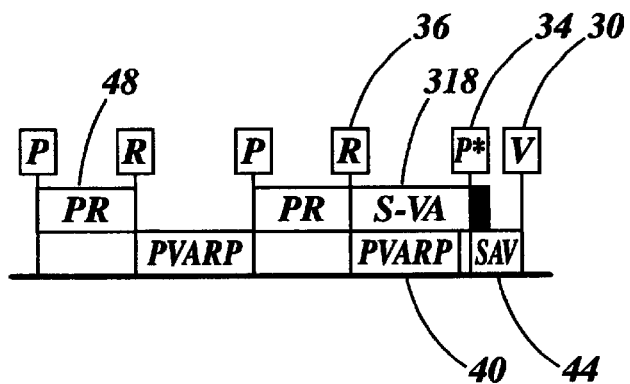
FIG. 43 is a plot showing ventricular tracking with the S-VA interval when a P-wave is sensed during the S-VA interval and after the end of PVARP.

FIG. 43 illustrates ventricular tracking utilizing the S-VA interval when a P-wave is sensed during the S-VA interval and after the end of PVARP. Ventricular tracking is triggered upon sensing the R-wave 36 which starts the S-VA interval 318. A P-wave 32 sense occurs before the end of the S-VA interval 318 and after the end of the PVARP interval 40. This causes the S-VA interval to be terminated and starts the SAV interval which ends with a ventricular pace 30. In this cycle, the normal atrial maximum tracking rate would apply and might delay the ventricular pace 30 to limit the ventricular pacing rate to be no faster than the AMTR.

In still another embodiment of ventricular tracking of the present invention, the S-VA interval is set equal to a fixed pre-programmed value. One possible value for the S-VA interval is to set it equal to the difference between the RV interval and the PAV interval (RV–PAP). This setting ensures that the fastest the ventricle can be paced is limited to the ventricular maximum tracking rate, which can be set equal to or less than the atrial maximum tracking rate. Other fixed values based on other programmable standard pacemaker timing intervals are possible.

Alternatively, the S-VA interval may be set dynamically to pace the atrium faster than the intrinsic atrial rate measured from previous cardiac cycles. For instance, the atrial rate can be determined by measuring the time interval between the previous sensed P-waves, or it can be determined from intrinsically conducted sensed R-waves. Then the S-VA interval is set at the start of each ventricular tracking cycle according to the following equation: $S\text{-}VA=PP-PR-d_4$, where PP is the measured intrinsic atrial rate interval, PR is the time delay from the preceding sensed P-wave to the subsequent sensed R-wave, and $d_4$ determines how much faster the atrium will be paced than the intrinsic atrial rate. Without limitation, $d_4$ may range between 10 to 400 milliseconds. In this embodiment, the dynamic S-VA interval could be limited to a pre-programmed minimum time, such as 350 to 1000 milliseconds. Alternatively, the S-VA interval can be set dynamically to pace the atrium at a constant pre-determined rate by the following equation: $S\text{-}VA=PA-PR$, where PR is the time delay from the preceding sensed P-wave to the subsequent sensed R-wave, and PA is the constant pre-determined atrial pacing rate interval. A possible rate range for PA is 60 to 180 bpm.

Figure 44:
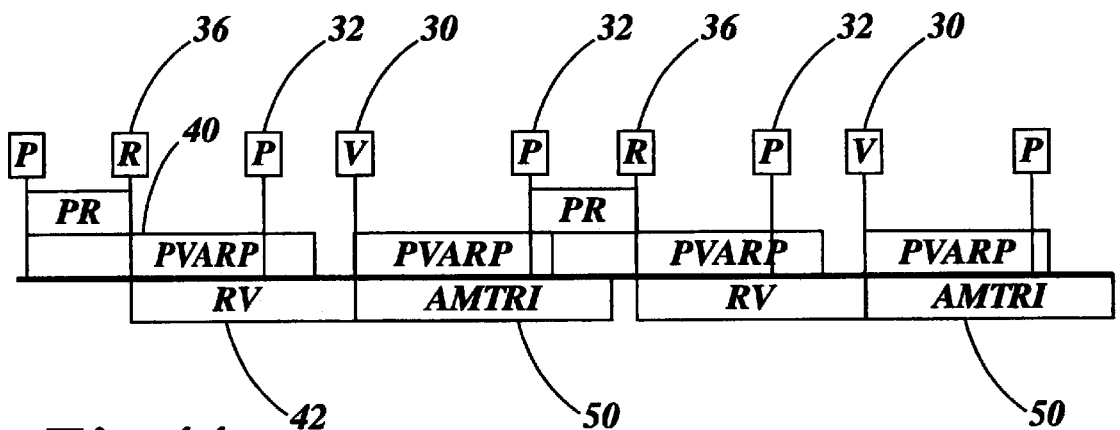
FIG. 44 is a plot showing ventricular rate oscillation occurring when there is 2:1 ventricular tracking when the atrial rate is less than AMTR.
Figure 45:
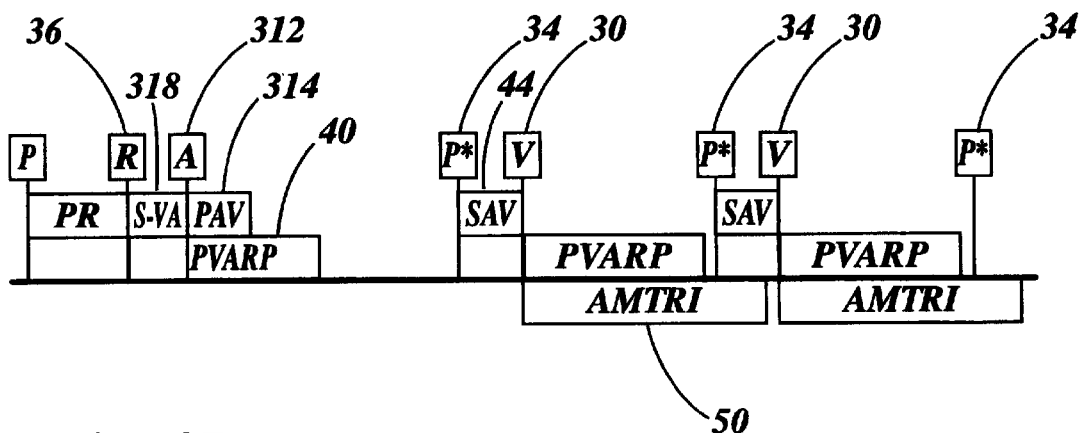
FIG. 45 is a plot showing ventricular tracking with a very short S-VA interval and modified PAV interval.

In still another embodiment, ventricular tracking with the S-VA interval may be utilized to avoid the ventricular rate oscillation that might occur with other versions of ventricular tracking when the atrial rate is below the AMTR. An example of ventricular rate oscillation with. rate priority ventricular tracking when the atrial rate is below the AMTR is shown in FIG. 44. This can be avoided with the embodiment of ventricular tracking with the S-VA interval by setting the S-VA interval very short so that atrial pacing occurs while the intrinsic atrio-ventricular conduction pathway is still refractory and thus will not conduct the atrial paced impulse into the ventricle, but it will cause the atrium to restart its natural rhythm cycle. An additional part of this embodiment is that the PAV interval is modified so that when it expires, it does not pace the ventricle, but it does terminate the ventricular tracking cycle and thus starts the next cardiac cycle with the normal atrial tracking intervals. This embodiment is illustrated in FIG. 45. One possible value range for the modified S-VA interval is 0 to 150 milliseconds. Alternatively, the modified S-VA interval can be set dynamically at the start of each ventricular tracking cycle to pace the atrium at a constant pre-determined rate by the equation described above: $S\text{-}VA=PA-PR$. In this embodiment, a possible interval range for PA is 250 to 350 milliseconds. Further, a backup stimulation to the atrium could be provided to ensure capture of the atrium. The backup pace would occur before the end of the PAV interval, thus, not affecting the other timing intervals.

FIG. 44 illustrates ventricular rate oscillation occurring when there is 2:1 ventricular tracking when the atrial rate is less than AMTR. The plot shows rate priority ventricular tracking triggered at the sensed R-wave 36. A P-wave 32 is sensed during PVARP 40 and during the RV 42 interval so a ventricular pace 30 is generated at the end of the RV interval and normal atrial tracking intervals are restored by the next cycle. The next P-wave 32 is sensed during PVARP so it is not tracked and it generates an intrinsic atrio-ventricular conduction and R-wave 36. This triggers another cycle of ventricular tracking, which repeats the events of the first cardiac cycle in the example.

FIG. 45 illustrates ventricular tracking with a very short S-VA interval and modified PAV interval 314. In this embodiment, the ventricular tracking cycle initiates a short S-VA interval 318 that ends with an atrial pace 312. This starts the PAV interval 314 which is modified so the ventricle is not paced when the PAV interval expires. However the ventricular tracking cycle ends when the PAV interval expires. In this example, the atrial pace 312 occurs when the atrio-ventricular conduction pathway is still refractory so a conduction from the paced atrium to the ventricle does not occur. However, the atrial pace causes the atrium to restart its rhythm cycle so that the next intrinsic conduction from the atrium is delayed until after the end of the PVARP interval 40. Since this intrinsic P-wave 32 is sensed after the end of PVARP, normal atrial tracking occurs.

This invention has been described herein in considerable detail in order to comply with the patent statutes and to provide those skilled in the art with the information needed to apply the novel principles and to construct and use such specialized components as are required. However, it is to be understood that the invention can be carried out by specifically different devices, and that various modifications, both as to the equipment details and operating procedures, can be accomplished without departing from the scope of the invention itself.

What is claimed is:

1. A cardiac rhythm management device for stimulating a ventricle of a patient's heart, said rhythm management device including:

(a) circuitry for sensing and tracking independently atrial and ventricular depolarization events over a plurality of programmed timing and pacing intervals, and transmitting signals corresponding to sensed and tracked atrial and ventricular events;

(b) a controller including an element for receiving signals corresponding to said sensed and tracked atrial and ventricular depolarization events and which is coupled to said plurality of programmed timing and pacing intervals, said controller having a preset ventricular tracking protocol, wherein said controller implementing said preset ventricular tracking protocol is capable of distinguishing during a cardiac cycle an intrinsic ventricular depolarization from ectopic depolarizations when an intrinsic atrial depolarization is sensed prior to the end of a preset preceding post ventricular atrial refractory period timing interval; and (c) wherein said ventricular tracking protocol includes delaying activation of said circuitry for ventricular tracking for a predetermined number of cardiac cycles before an intrinsic ventricular depolarization event is sensed wherein said protocol avoids ventricular rate oscillation.

2. A cardiac rhythm management device for stimulating a ventricle of a patient's heart, said rhythm management device including:

(a) circuitry for sensing and tracking independently atrial and ventricular depolarization events over a plurality of programmed timing and pacing intervals, and transmitting signals corresponding to sensed and tracked atrial and ventricular events;

(b) a controller including an element for receiving signals corresponding to said sensed and tracked atrial and ventricular depolarization events and which is coupled to said plurality of programmed timing and pacing intervals, said controller having a preset ventricular tracking protocol, wherein said controller implementing said preset ventricular tracking protocol is capable of distinguishing during a cardiac cycle an intrinsic ventricular depolarization from ectopic depolarizations when an intrinsic atrial depolarization is sensed prior to the end of a preset preceding post ventricular atrial refractory period timing interval; and (c) wherein said ventricular tracking protocol includes delaying activation of said circuitry for ventricular tracking for a predetermined number of cardiac cycles after an intrinsic ventricular depolarization event is sensed wherein said protocol avoids ventricular rate oscillation.

* * * * *